(12) United States Patent
Goodrich et al.

(10) Patent No.: US 7,498,156 B2
(45) Date of Patent: *Mar. 3, 2009

(54) USE OF VISIBLE LIGHT AT WAVELENGTHS OF 500 TO 550 NM TO REDUCE THE NUMBER OF PATHOGENS IN BLOOD AND BLOOD COMPONENTS

(75) Inventors: Raymond P. Goodrich, Lakewood, CO (US); Matthew S. Platz, Columbus, OH (US); Christopher B. Martin, Beaumont, TX (US)

(73) Assignees: CaridianBCT Biotechnologies, LLC, Lakewood, CO (US); Ohio State University Research Foundation, Columbus, OH (US)

(*) Notice: Subject to any disclaimer, the term of this patent is extended or adjusted under 35 U.S.C. 154(b) by 341 days.

This patent is subject to a terminal disclaimer.

(21) Appl. No.: 11/154,503

(22) Filed: Jun. 15, 2005

(65) Prior Publication Data

US 2005/0282143 A1 Dec. 22, 2005

Related U.S. Application Data

(63) Continuation-in-part of application No. 10/377,524, filed on Feb. 28, 2003, which is a continuation of application No. 09/586,147, filed on Jun. 2, 2000, now abandoned, which is a continuation-in-part of application No. 09/357,188, filed on Jul. 20, 1999, now Pat. No. 6,277,337, which is a continuation-in-part of application No. 09/119,666, filed on Jul. 21, 1998, now Pat. No. 6,258,577.

(60) Provisional application No. 60/580,311, filed on Jun. 15, 2004.

(51) Int. Cl.
*C12N 13/00* (2006.01)
*A61K 35/14* (2006.01)
*A61K 31/525* (2006.01)

(52) U.S. Cl. .................. 435/173.1; 514/251; 424/529

(58) Field of Classification Search .............. 435/2, 435/251, 173.1; 514/251; 424/529–534
See application file for complete search history.

(56) References Cited

U.S. PATENT DOCUMENTS

| | | | |
|---|---|---|---|
| 683,690 A | 10/1901 | Johnson |
| 1,733,239 A | 10/1929 | Roberts |
| 1,961,700 A | 6/1934 | Moehler |
| 2,056,614 A | 10/1936 | Moehler |
| 2,212,230 A | 8/1940 | Goldmann |
| 2,212,330 A | 8/1940 | Thomas |
| 2,340,890 A | 2/1944 | Lang et al. |
| 2,786,014 A | 3/1957 | Tullis |
| 3,456,053 A | 7/1969 | Crawford |
| 3,629,071 A | 12/1971 | Sekhar |
| 3,683,177 A | 8/1972 | Veloz |
| 3,683,183 A | 8/1972 | Vizzini et al. |
| 3,705,985 A | 12/1972 | Manning et al. |
| 3,776,694 A | 12/1973 | Leittl |
| 3,852,032 A | 12/1974 | Urbach |
| 3,864,081 A | 2/1975 | Logrippo |
| 3,874,384 A | 4/1975 | Deindoerfer et al. |
| 3,894,236 A | 7/1975 | Hazelrigg |
| 3,926,556 A | 12/1975 | Boucher |
| 3,927,325 A | 12/1975 | Hungate et al. |
| 4,061,537 A | 12/1977 | Seiler et al. |
| 4,112,070 A | 9/1978 | Harmening |
| 4,124,598 A | 11/1978 | Hearst et al. |
| 4,139,348 A | 2/1979 | Swartz |
| 4,169,204 A | 9/1979 | Hearst et al. |
| 4,173,631 A | 11/1979 | Graham et al. |
| 4,181,128 A | 1/1980 | Swartz |
| 4,196,281 A | 4/1980 | Hearst et al. |
| 4,264,601 A | 4/1981 | Trachewsky |
| 4,267,269 A | 5/1981 | Grode et al. |
| 4,312,883 A | 1/1982 | Baccichetti et al. |
| 4,321,918 A | 3/1982 | Clark, II |
| 4,321,919 A | 3/1982 | Edelson |
| 4,336,809 A | 6/1982 | Clark |
| 4,390,619 A | 6/1983 | Harmening-Pittiglio |
| 4,398,031 A | 8/1983 | Bender et al. |
| 4,398,906 A | 8/1983 | Edelson |
| 4,402,318 A | 9/1983 | Swartz |
| 4,407,282 A | 10/1983 | Swartz |
| 4,421,987 A | 12/1983 | Herold |
| 4,424,201 A | 1/1984 | Valinsky et al. |
| 4,428,744 A | 1/1984 | Edelson |
| 4,432,750 A | 2/1984 | Estep |
| 4,456,512 A | 6/1984 | Bieler et al. |
| 4,457,918 A | 7/1984 | Holick et al. |

(Continued)

FOREIGN PATENT DOCUMENTS

EP 0066886 6/1982

(Continued)

OTHER PUBLICATIONS

Martin et al. "An action spectrum of the riboflavin-photosensitized inactivation of Lambda phage" Photochem. Photobiol. (Mar./Apr. 2005) 81:474-480.*

(Continued)

*Primary Examiner*—Sandra Saucier
*Assistant Examiner*—Susan Hanley
(74) *Attorney, Agent, or Firm*—Laura Butterfield Arciniegas; Edna M. O'Connor; John R. Merkling

(57) ABSTRACT

This invention is directed towards a method of using visible light at wavelengths of at least 500 nm and above in combination with a sensitizer having a flavin moiety to reduce any pathogens that may be contained in blood and blood components. By exposing the blood and blood components to light of 500 nm and higher, only the sensitizer that is bound to nucleic acids of the pathogens will be activated, thus destroying the sensitizer-pathogenic nucleic acid complex. Because unbound sensitizer is not activated at this wavelength, damage to blood and blood components caused by photolysis of unbound sensitizer may be avoided.

10 Claims, 7 Drawing Sheets

U.S. PATENT DOCUMENTS

| | | |
|---|---|---|
| 4,464,166 A | 8/1984 | Edelson |
| 4,467,206 A | 8/1984 | Taylor et al. |
| 4,474,153 A | 10/1984 | Rock et al. |
| 4,481,167 A | 11/1984 | Ginter et al. |
| 4,493,981 A | 1/1985 | Payne |
| 4,568,328 A | 2/1986 | King |
| 4,572,899 A | 2/1986 | Walker et al. |
| 4,573,960 A | 3/1986 | Goss |
| 4,573,961 A | 3/1986 | King |
| 4,573,962 A | 3/1986 | Troutner |
| 4,576,143 A | 3/1986 | Clark, III |
| 4,578,056 A | 3/1986 | King et al. |
| 4,585,735 A | 4/1986 | Meryman et al. |
| 4,596,547 A | 6/1986 | Troutner |
| 4,604,356 A | 8/1986 | Blake, II |
| 4,608,255 A | 8/1986 | Kahn et al. |
| 4,609,372 A | 9/1986 | Carmen et al. |
| 4,612,007 A | 9/1986 | Edelson |
| 4,613,322 A | 9/1986 | Edelson |
| 4,614,190 A | 9/1986 | Stanco et al. |
| 4,623,328 A | 11/1986 | Hartranft |
| 4,626,431 A | 12/1986 | Batchelor et al. |
| 4,642,171 A | 2/1987 | Sekine et al. |
| 4,645,649 A | 2/1987 | Nagao |
| 4,648,992 A | 3/1987 | Graf et al. |
| 4,649,151 A | 3/1987 | Dougherty et al. |
| 4,651,739 A | 3/1987 | Oseroff et al. |
| 4,675,185 A | 6/1987 | Kandler et al. |
| 4,683,195 A | 7/1987 | Mullis et al. |
| 4,683,202 A | 7/1987 | Mullis |
| 4,683,889 A | 8/1987 | Edelson |
| 4,684,521 A | 8/1987 | Edelson |
| 4,693,981 A | 9/1987 | Wiesehahn et al. |
| 4,695,460 A | 9/1987 | Holme |
| 4,704,352 A | 11/1987 | Miripol et al. |
| 4,708,715 A | 11/1987 | Troutner et al. |
| 4,726,949 A | 2/1988 | Miripol et al. |
| 4,727,027 A | 2/1988 | Wiesehahn et al. |
| 4,737,140 A | 4/1988 | Lee et al. |
| 4,748,120 A | 5/1988 | Wiesehahn |
| 4,769,318 A | 9/1988 | Hamasaki et al. |
| 4,775,625 A | 10/1988 | Sieber |
| 4,788,038 A | 11/1988 | Matsunaga |
| RE32,874 E | 2/1989 | Rock et al. |
| 4,828,976 A | 5/1989 | Murphy |
| 4,831,268 A | 5/1989 | Fisch et al. |
| 4,833,165 A | 5/1989 | Louderback |
| 4,861,704 A | 8/1989 | Reemtsma et al. |
| 4,866,282 A | 9/1989 | Miripol et al. |
| 4,878,891 A | 11/1989 | Judy et al. |
| 4,880,788 A | 11/1989 | Moake et al. |
| 4,915,683 A | 4/1990 | Sieber |
| 4,921,473 A | 5/1990 | Lee et al. |
| 4,925,665 A | 5/1990 | Murphy |
| 4,930,516 A | 6/1990 | Alfano et al. |
| 4,946,438 A | 8/1990 | Reemtsma et al. |
| 4,948,980 A | 8/1990 | Wedekamp |
| 4,950,665 A | 8/1990 | Floyd |
| 4,952,812 A | 8/1990 | Miripol et al. |
| 4,960,408 A | 10/1990 | Klainer et al. |
| 4,961,928 A | 10/1990 | Holme et al. |
| 4,978,688 A | 12/1990 | Louderback |
| 4,986,628 A | 1/1991 | Lozhenko et al. |
| 4,992,363 A | 2/1991 | Murphy |
| 4,994,367 A | 2/1991 | Bode et al. |
| 4,998,931 A | 3/1991 | Slichter et al. |
| 4,999,375 A | 3/1991 | Bachynsky et al. |
| 5,011,695 A | 4/1991 | Dichtelmuller et al. |
| 5,017,338 A | 5/1991 | Surgenor |
| 5,020,995 A | 6/1991 | Levy |
| 5,030,200 A | 7/1991 | Judy et al. |
| 5,039,483 A | 8/1991 | Sieber et al. |
| 5,041,078 A | 8/1991 | Matthews et al. |
| 5,089,146 A | 2/1992 | Carmen et al. |
| 5,089,384 A | 2/1992 | Hale |
| 5,092,773 A | 3/1992 | Levy |
| 5,114,670 A | 5/1992 | Duffey |
| 5,114,957 A | 5/1992 | Hendler et al. |
| 5,120,649 A | 6/1992 | Horowitz et al. |
| 5,123,902 A | 6/1992 | Müller et al. |
| 5,133,932 A | 7/1992 | Gunn et al. |
| 5,147,776 A | 9/1992 | Koerner, Jr. |
| 5,149,718 A | 9/1992 | Meruelo et al. |
| 5,150,705 A | 9/1992 | Stinson |
| 5,166,528 A | 11/1992 | Le Vay |
| 5,184,020 A | 2/1993 | Hearst et al. |
| 5,185,532 A | 2/1993 | Zabsky et al. |
| 5,192,264 A | 3/1993 | Fossel |
| 5,211,960 A | 5/1993 | Babior |
| 5,216,251 A | 6/1993 | Matschke |
| 5,229,081 A | 7/1993 | Suda |
| 5,232,844 A | 8/1993 | Horowitz et al. |
| 5,234,808 A | 8/1993 | Murphy |
| 5,236,716 A | 8/1993 | Carmen et al. |
| 5,247,178 A | 9/1993 | Ury et al. |
| 5,248,506 A | 9/1993 | Holme et al. |
| 5,250,303 A | 10/1993 | Meryman et al. |
| 5,258,124 A | 11/1993 | Bolton et al. |
| 5,269,946 A | 12/1993 | Goldhaber et al. |
| 5,273,713 A | 12/1993 | Levy |
| 5,281,392 A | 1/1994 | Rubinstein |
| 5,288,605 A | 2/1994 | Lin et al. |
| 5,288,647 A | 2/1994 | Zimlich, Jr. et al. |
| 5,290,221 A | 3/1994 | Wolf, Jr. et al. |
| 5,300,019 A | 4/1994 | Bischof et al. |
| 5,304,113 A | 4/1994 | Sieber et al. |
| 5,318,023 A | 6/1994 | Vari et al. |
| 5,340,716 A | 8/1994 | Ullman et al. |
| 5,342,752 A | 8/1994 | Platz et al. |
| 5,344,752 A | 9/1994 | Murphy |
| 5,344,918 A | 9/1994 | Dazey et al. |
| 5,358,844 A | 10/1994 | Stossel et al. |
| 5,360,734 A | 11/1994 | Chapman et al. |
| 5,366,440 A | 11/1994 | Fossel |
| 5,376,524 A | 12/1994 | Murphy et al. |
| 5,378,601 A | 1/1995 | Gepner-Puszkin |
| 5,418,130 A | 5/1995 | Platz et al. |
| 5,419,759 A | 5/1995 | Naficy |
| 5,427,695 A | 6/1995 | Brown |
| 5,433,738 A | 7/1995 | Stinson |
| 5,459,030 A | 10/1995 | Lin et al. |
| 5,466,573 A | 11/1995 | Murphy et al. |
| 5,474,891 A | 12/1995 | Murphy |
| 5,482,828 A | 1/1996 | Lin et al. |
| 5,487,971 A | 1/1996 | Holme et al. |
| 5,494,590 A | 2/1996 | Smith et al. |
| 5,503,721 A | 4/1996 | Hearst et al. |
| 5,512,187 A | 4/1996 | Buchholz et al. |
| 5,516,629 A | 5/1996 | Park et al. |
| 5,527,704 A | 6/1996 | Wolf, Jr. et al. |
| 5,536,238 A | 7/1996 | Bischof |
| 5,545,516 A | 8/1996 | Wagner |
| 5,547,635 A | 8/1996 | Duthie, Jr. |
| 5,550,111 A | 8/1996 | Suhadolnik et al. |
| 5,556,958 A | 9/1996 | Carroll et al. |
| 5,556,993 A | 9/1996 | Wollowitz et al. |
| 5,557,098 A | 9/1996 | D'Silva |
| 5,569,579 A | 10/1996 | Murphy |
| 5,571,666 A | 11/1996 | Floyd et al. |
| 5,587,490 A | 12/1996 | Goodrich, Jr. et al. |
| 5,593,823 A | 1/1997 | Wollowitz et al. |
| 5,597,722 A | 1/1997 | Chapman et al. |
| 5,607,924 A | 3/1997 | Magda et al. |
| 5,622,867 A | 4/1997 | Livesey et al. |

| | | |
|---|---|---|
| 5,624,435 A | 4/1997 | Furumoto et al. |
| 5,624,794 A | 4/1997 | Bitensky et al. |
| 5,628,727 A | 5/1997 | Hakky et al. |
| 5,639,376 A | 6/1997 | Lee et al. |
| 5,639,382 A | 6/1997 | Brown |
| 5,643,334 A | 7/1997 | Eckhouse et al. |
| 5,652,096 A | 7/1997 | Cimino |
| 5,653,887 A | 8/1997 | Wahl et al. |
| 5,654,443 A | 8/1997 | Wollowitz et al. |
| 5,656,154 A | 8/1997 | Meryman |
| 5,656,498 A | 8/1997 | Iijima et al. |
| 5,658,530 A | 8/1997 | Dunn |
| 5,658,722 A | 8/1997 | Margolis-Nunno et al. |
| 5,683,661 A | 11/1997 | Hearst et al. |
| 5,683,768 A | 11/1997 | Shang et al. |
| 5,686,436 A | 11/1997 | Van Dyke |
| 5,688,475 A | 11/1997 | Duthie, Jr. |
| 5,691,132 A | 11/1997 | Wollowitz et al. |
| 5,698,524 A | 12/1997 | Mach et al. |
| 5,698,677 A | 12/1997 | Eibl et al. |
| 5,702,684 A | 12/1997 | McCoy et al. |
| 5,707,401 A | 1/1998 | Talmore |
| 5,709,653 A | 1/1998 | Leone |
| 5,709,991 A | 1/1998 | Lin et al. |
| 5,709,992 A | 1/1998 | Rubinstein |
| 5,712,085 A | 1/1998 | Wollowitz et al. |
| 5,712,086 A | 1/1998 | Horowitz et al. |
| 5,714,328 A | 2/1998 | Magda et al. |
| 5,736,313 A | 4/1998 | Spargo et al. |
| 5,739,013 A | 4/1998 | Budowsky et al. |
| 5,753,428 A | 5/1998 | Yuasa et al. |
| 5,756,553 A | 5/1998 | Iguchi et al. |
| 5,769,839 A | 6/1998 | Carmen et al. |
| 5,772,960 A | 6/1998 | Ito et al. |
| 5,783,093 A | 7/1998 | Holme |
| 5,789,150 A | 8/1998 | Margolis-Nunno et al. |
| 5,789,151 A | 8/1998 | Bitensky et al. |
| 5,789,601 A | 8/1998 | Park et al. |
| 5,798,238 A | 8/1998 | Goodrich, Jr. et al. |
| 5,798,523 A | 8/1998 | Villeneuve et al. |
| 5,817,519 A | 10/1998 | Zelmanovic et al. |
| 5,827,644 A | 10/1998 | Floyd et al. |
| 5,834,198 A | 11/1998 | Famulok et al. |
| 5,840,252 A | 11/1998 | Giertych |
| 5,843,459 A | 12/1998 | Wang et al. |
| 5,846,961 A | 12/1998 | Van Dyke |
| 5,854,967 A | 12/1998 | Hearst et al. |
| 5,866,074 A | 2/1999 | Chapman et al. |
| 5,869,701 A | 2/1999 | Park et al. |
| 5,871,900 A | 2/1999 | Wollowitz et al. |
| 5,876,676 A | 3/1999 | Stossel et al. |
| 5,899,874 A | 5/1999 | Jonsson |
| 5,906,915 A | 5/1999 | Payrat et al. |
| 5,908,742 A | 6/1999 | Lin et al. |
| 5,919,614 A | 7/1999 | Livesey et al. |
| 5,922,278 A | 7/1999 | Chapman et al. |
| 5,935,092 A | 8/1999 | Sun et al. |
| 5,955,256 A | 9/1999 | Sowemimo-Coker et al. |
| 5,955,257 A | 9/1999 | Burger et al. |
| 5,965,349 A | 10/1999 | Lin et al. |
| 5,976,884 A | 11/1999 | Chapman et al. |
| 6,017,691 A | 1/2000 | Wollowitz et al. |
| 6,020,333 A | 2/2000 | Berque |
| 6,060,233 A | 5/2000 | Wiggins |
| 6,063,624 A | 5/2000 | Kandler et al. |
| 6,087,141 A | 7/2000 | Margolis-Nunno et al. |
| 7,094,378 B1 * | 8/2006 | Goodrich et al. ............ 422/22 |

FOREIGN PATENT DOCUMENTS

| | | |
|---|---|---|
| EP | 0124 363 | 4/1984 |
| EP | 0108 588 | 5/1984 |
| EP | 0196 515 A1 | 3/1986 |
| EP | 0184 331 A2 | 6/1986 |
| EP | 0491 757 | 9/1990 |
| EP | 0525 138 B1 | 12/1991 |
| EP | 0590 514 A1 | 4/1994 |
| EP | 0679 398 A1 | 11/1995 |
| EP | 0510 185 B1 | 12/1996 |
| EP | 0754 461 A2 | 1/1997 |
| EP | 0801 072 A2 | 10/1997 |
| FR | 2674 753 | 10/1992 |
| FR | 2715 303 | 7/1995 |
| FR | 2718 353 | 10/1995 |
| GB | 2034463 A | 6/1980 |
| WO | WO 83/02328 | 7/1983 |
| WO | WO 85/02116 | 5/1985 |
| WO | WO 89/06702 | 7/1989 |
| WO | WO 90/00059 | 1/1990 |
| WO | WO 91/02529 | 3/1991 |
| WO | WO 92/08348 | 5/1992 |
| WO | WO 92/08349 | 5/1992 |
| WO | WO 92/11057 | 7/1992 |
| WO | WO 92/17173 | 10/1992 |
| WO | WO 93/00005 | 1/1993 |
| WO | WO 94/07426 | 4/1994 |
| WO | WO 94/07499 | 4/1994 |
| WO | WO 95/02325 | 1/1995 |
| WO | WO 95/11028 | 4/1995 |
| WO | WO 95/12973 | 5/1995 |
| WO | WO 95/16348 | 6/1995 |
| WO | WO 96/14740 | 5/1996 |
| WO | WO 96/14741 | 5/1996 |
| WO | WO 97/07674 | 3/1997 |
| WO | WO 97/18844 | 5/1997 |
| WO | WO 97/22245 | 6/1997 |
| WO | WO 97/36581 | 10/1997 |
| WO | WO 97/36634 | 10/1997 |
| WO | WO 98/30545 | 7/1998 |
| WO | WO 98/31219 | 7/1998 |
| WO | WO 98/41087 | 9/1998 |
| WO | WO 98/51147 | 11/1998 |
| WO | WO 98/56247 | 12/1998 |
| WO | WO 99/11305 | 3/1999 |
| WO | WO 99/59645 | 11/1999 |
| WO | WO 00/11946 | 9/2000 |
| WO | WO 01/28599 | 4/2001 |

OTHER PUBLICATIONS

Ahmad et al, "Alkaline Hydrolysis of 7,8-Dimethyl-10(formylmethyl)isoalloxazine. A Kinetic Study", *J. of Organic Chemistry*, 1980, 45:731-733.

Beaumont et al, "Singlet Oxygen Production by some Furocoumarin Derivatives in the Presence of DNA: Time Resolved Luminescence Measurements", *Photochem. Photobiol.*, 1985, 42:605-608.

Ben-Hur et al, "Advanced in Photochemical Approaches for Blood Sterilization", *Photochem., Photobiol*, 1995, 62:383-388.

Bockstahler et al, "Ultraviolet Light Enhanced Reactivation of a Mamalian Virus", *Biochem, Biophsys Res. Commun*, 1970, 41:184-189.

Broughton et al, "Effect of Blue Light on Hyperbilirubinanemia", *Arch., Dis. Childh.*, 1963, 40:666-671.

Burch et al, "Fluorometric Measurements of Riboflavin and its Natural Derivatives in small Quantities of Blood Serum and Cells", *J. Biol. Chem.*, 1948, 457-480.

Burger et al, "Mutagenicity of 8-Methoxypsoralen and Long-wave Ultraviolet Irradiation in Diploid Human Skin Fibroblasts An Improved Risk Estimate in Photochemotherapy", *Mutation Research.*, 1979, 63:371-380.

Busch et al, "Current and Emerging Infectious Risks of Blood Transfusions", *JAMA*, 2003, 289:959-961.

Busch et al, "NAT and Blood Safety: What is the Paradigm?", *Transfusion*, 2000, 40:1157-1160.

Busch, et al, "Closing the Windows on Viral Transmission by Blood Transfusion", *Blood Safety in the New Millennium: AABB 2000*

*Emily Cooley Seminar Book*, S.L. Stamner, ed, AABB Press, Bethesda, Maryland, 2001, pp. 33-54.

Coohill, T.P., "Action Spectroscopy: Ultraviolet Radiation", in *CRC Handbook of Organic Photochemistry and Photobiology*, W. M. Horspool, ed., CRC Press, Boca Raton, 1995, 1267-1275.

Cortes et al, "Both Cross-links and Monoadducts Induced in NA by Psoralens can Lead to Sister Chromatid Exchange Formation", *Exptl. Cell. Res.*, 1991, 196:127-130.

Cumming, et al, "Exposure of Patients to Human Immunodeficiency Virus through the Transfusion of Blood Components that Test Antibody-negative", *N. Eng. J. Med*, 1989, 321:941-946.

Dardare et al, "Binding Affinities of Commonly Employed Sensitizers of Viral Inactivation", *Photochemistry and Photobiology*, 2002, 75(6): 561-564.

Daubeny, Charles, "On the Action of Light upon Plants, and of Plants upon the Atmosphere", *Philosophical. Transactions of the Royal Society of London, Series B*, 1836, pp. 149-179.

De Mol et al, "Singlet Oxygen Formation by Sensitization of Furocoumarins Complexed with, or Bound Covalently to DNA", *Photochem. Photobiol.* 1981, 34:661-666.

Dodd et al, "Inactivation of viruses in platelet suspensions that retain their in vitro characteristics: comparison of psoralen-ultraviolet A and merocynanine 540-visible light methods", *Transfusion*, vol. 31, No. 6, 1991, pp. 483-490.

Dye et al, "Repair of phage λ DNA damaged by near ultraviolet light plus 8-methoxypsoralen", *J. Gen. Virol*, 1995, 76:723-726.

Edwards et al, "Visible light effects on tumoral cells in a culture medium enriched with tryptophan and riboflavin", *Photochem. Photobiol B.Biol.*, 1994, 24:179-186.

Ennever et al. (1983), "Potential for Genetic Damage from Multivitamin Solutions Exposed to Phototherapy Illumination," *Pediatr. Res.* 17:192-194.

Gates, F.L., "A Study of the bactericidal action of Ultra Violet Light", *J. Gen Physiol.*, 1930, 14:31-42.

Gromisch et al, "Light (phototherapy)-induced riboflavin deficiency in the neonate", *J. Ped.*, 1977, 90:118-122.

Heelis, P.F., "The Photochemistry of Flavins", *Chemistry and Biochemistry of Flavoenzymes*, ed. Franz Muller, CRC Press, 1991, Boca Raton, vol. I, chap. 5, pp. 171-193.

Heelis, P.F., "The Photophysical and Photochemical Properties of Flavins (Isoalloxazines)", *Chem. Soc., Rev.*, 1982, 11:15-39.

Jacques, P.F., "Nutritional Antioxidants and Prevention of Age-related Eye Diseasebn", *Antioxid. Dis. Prev.*, 1997, 149-177.

Jazzar et al, "Genotoxicity of Photoilluminated Riboflavin in the Presence of Cu(II)", *Free Radical Biology & Medicine*, 1996, 21:7-14.

Joshi, P.C., Ultraviolet radiation-induced photodegradation and $O_2O_2$ production by riboflavin, lumichrome and lumiflavin, *Ind. J. Biochem. Biophys.*, 1989, 26:186-189.

Kanne et al, "Isolation and Characterization of Pyrimidine-psoralen-pyrimidine Photodiadducts from DNA", *J. Am., Chem. Soc.*, 1982, 104:6754-6764.

Kasturi et al, "Inactivation of Lambda Phage with 658 nm Light using a DNA Binding Porphyrin Sensitizer", *Photochem Photobiol.*, 1992, 56:427-429.

Kleczkowski, A., "Action Spectra and Their Interpretation", in *Research Progress in Organic Biological and Medicinal Chemistry*, Gallo et al, eds., North Holland Publishing, American Publishing, New York, 1972, pp. 48-70.

Lambrecht et al, "Photoinactivation of Viruses in Human Fresh Plasma by Phenothiazine Dyes in Combination with Visible Light", *Vox Sang.* 1991, 60:207-213.

Lin et al, "Photochemical inactivation of viruses and bacteria in platelet concentrates by use of a novel psoralen and long-wavelength ultraviolet light", *Transfusion*, 1997, 37:423.

Lin et al, "Use of 8-Methoxypsoralen and Long-Wavelength Ultraviolet Radiation for Decontamination of Platelet Concentrates", *Blood*, vol. 74, No. 1, 1989, pp. 517-547.

Lipson, E.D., "Action Spectroscopy: Methodology", in *CRC Handbook of Organic Photochemistry and Photobiology*, W.M. Horspool, ed., CRC Press, Boca Raton, 1995, 1257-1266.

Lytle et al, "Infection of UV-irradiated Xeroderma Pigmentosum Fibroblasts by Herpes Simplex Virus: Study of Capacity and Weigle Reactivation", *Mutat. Res.*, 1976, 36:257-264.

Mak et al, "Design and Synthesis of broad-based Mono- and Bi-cyclic Inhibitors of FIV and HIV Proteases", *Bioorganic & Medicinal Chem.*, 2003, 11:2025-2040.

Marley et al, "A New Photoproduct from Furocoumarin Photolysis in Dilute Aqueous Solution: 5-Formyl-6hydroxybenzofuran", *Photochem. Photobiol*, 1994, 59:503-505.

Miolo et al, 4',5'-subtituted Methylangelicins: Photocycloadducts with Pyrimidijne Bases of DNA, *Photochemistry and Photobiology*, vol. 59, No. 3, 1994, pp. 277-283.

Mitchell, D.L., "DNA Damage and Repair", in in *CRC Handbook of Organic Photochemistry and Photobiology*, W.M. Horspool, ed., CRC Press, Boca Raton, 1995, 1326-1331.

Moor et al, "Biochemical Aspects of Psoralen Photochemotherapy", *Clinics in Derm.*, 1996, 14:353-365.

Müller-Breitkreutz et al, "Inactivation of Viruses by Chemically and Photochemicaly Generated Singlet Molecular Oxygen", *Photochem. Photobiol B: Biology*, 1995, 30:63-70.

Nogami. et al, "Pharmacokinetic Aspects of Biliary Excretion. Dose Dependency of Riboflavin in Rat," *Chem. Pharm. Bull.*, 1970, 18:228-234.

Ono et al, "Effects of Aging on the Formation of Ester Forms of Riboflavin in the Rat Lens," *Internat. J. Vit. Nutr. Res.*, 1986, 56:259-262.

Papodopoulu et al, "Genotoxic effects and DNA photoadducts induced in Chinese hamster V79 cells by 5-methoxypsoralen and 8-methoxypsoralen", *Mut. Res.*, 1985, 151:281-291.

Petersen et al, "Duration of time from onset of human immunodeficiency virus type 1 infectiousness to development of detectable antibody", *Transfusion*, 1994, 34:283-289.

Prince et al, "The Development of Virus-Free Labile Blood Derivatives—A Review," *Eur. J. Epidemionol*, 0392-2990, vol. 3, No. 2, Jun. 1987, pp. 103-118, 1987.

Qian et al, "$C_2$-Symmetrical Tetrahydroxyazepanes as Inhibitors of Glycosidases and HIV/FIV Proteases", *Bioorgani & Medicinal Chem.*, 1996, 4:2055-2069.

Rhodes et al, "Therapeutic potentiation of the immune system by costimulatory Schiff-base-forming drugs", *Nature*, 1995, 377:71-75.

Rivlin, R.S., "Riboflavin Metabolism," *New Engl. J. Med.*, 1970, 283(9): 463-472.

Schmunis, G.A., "*Trypansoma cruzi*, the etiologic agent of Chagas' disease: status in the blood supply in endemic and nonendemic countries", *Transfusion*, 1992, 31:547-557.

Silva et al., "Riboflavin-sensitized photoprocesses of tryptophan," *J. Photochem. Photobiol. B: Biol.* 23:43-48:1994.

Silva. et al, "A light-Induced Tryptophan-Riboflavin Binding: Biological Implications," in *Nutritional and Toxicological Consequences of Food Processing*, M. Friedman, ed., Plenum Press, New York, 1991, pp. 33-48.

Sisson, et al, "Effect of Broad and Narrow Spectrum Fluorescent Light on Blood Constituents", *Birth Defects*, 1976, XII:122-133.

Sisson, T.R.C., "Photodegradation of riboflavin in neonates", *Fed. Proc.*, 1987, 46:1883-1885.

Skripchenko et al, "Comparison of Methylene Blue and Methylene Violet for Photoinactivation of Intracellular and Extracellular Virus in Red Cell Suspensions", *J. Photochem. Photobiol.*, 1997, 65:451-455.

Smith, E.C. et al, "The Photochemical Degradation of Riboflavin," *J. Am. Chem. Soc.*, 1963, 85:3285-3288.

Specht et al, "A New Biological Target of Furocoumarins: Photochemical Formation of Covalent Adducts with Unsaturated Fatty Acids", *Photochem. Photobiol.*, 1988, 47, 537-541.

Stern et l, "Non-Melanoma Skin Cancer Occurring in Patients Treated with PUVA five to ten Years after First Treatment", *J. Invest. Dermatol*, 1998:120-124.

Stramer et al, "NAT of the United States and Canadian Blood Supply", *Transfusion*, 2000, 40:1165-1168.

Straub et al, "Isolation and Characterization of Pyrimidine-Psoralen Photoadducts from DNA", *J. Am. Chem Soc.*, 1981, 103:2347-2353.

Tapia et al, "Photo-induced riboflavin binding to the tryptophan residues", *Radiat. Environ. Biophys.*, 1991, 30:131-138.

Von Heneguawen, et al, "A method for the determination of PUVA-induced in vivo irrevrsible binding of 8-methoxypsoralen (8-MOP) to epidermal lipids, proteins and DNA/RNA", *J. Photochem. Photobiol B. Biol.*, 1989, 3:631-635.

Wagner et al, "Determination of Residual 4'-aminomethyl-4,5',8-trimethylpsoralen and Mutagenicity Testing following Psoralen Plus UVA Treatment of Platelet Suspensions", *Photochemistry and Photobiology*, vol. 57, No. 5, pp. 819-824, 1993.

Wasserman et al, "The Photooxidation of 8-Methoxypsoralen", *Photochem. Photobiol*, 1982, 35:565-567.

Wernert, G.T. "Chemotherapy and the magic bullet", *Chem. Aust.*, 1996, 226-227.

Wernert, G.T., "Paul Erlich—The man and his sicience" *Chem. Aust.*, 1997, 36-39.

Abdursashidova et al, "Polynucleotide-protein interactions in the translation system. Identification of proteins interacting with tRNA in the A- and P-sites of *E. coli* ribosomes," 1979 *Nucleic Acids Res.* 6(12):3891-3 909.

Belikov et al., "Choice of an Effective Method of Analysis of Riboflavin and Study of its Stability", 1988, *Farmatsiya*, 37(2), 39-41 in *DRUGU*, AN 1988-39621.

Budowsky, E. I, "Problems and Prospects for Preparation of Killed Antiviral Vaccines", 1991, *Adv. Virus Res.* 39: 255-290.

Budowsky et al "Polynucleotide-Protein Cross-Links Induced by Ultraviolet Light and Their Use for Structural Investigation of Nucleoproteins," 1989, *Progress in Nucleic Acids Res. And Mol. Bio* 37:1-65.

Budowsky et al, "Preparation of cyclic 2',3'-monophosphates of oligoadenylates (A2'p)nA>p and A3'p(A2'p)n-1A>p", *Eur. J. Biochem.*, 1994, 220:97-104.

Budowsky et al, "Principles of selective inactivation of viral genome. VI, Inactivation of the infectivity of the influenza virus by the action of β-propiolactone", *Vaccine*, 1991, 9:398-402.

Budowsky et al, "Principles of selective inactivation of viral genome. VII, Some peculiarities in determination of viral suspension infectivity during inactivation by chemical agents,", 1991, *Vaccine* 9:473-476.

Budowsky et al, "Principles of selective inactivation of viral genome. VIII, The influence of β-propiolactone on immunogenic and protective activities of influenza virus,", 1993, *Vaccine* 11(3):343-348.

Cadet et al., "Mechanisms and Products of Photosensitized Degradation of Nucleic Acids and Related Model Compounds," 1983, *Israel J. Chem.* 23:420-429.

Chow et al, "Recognition of G-U mismatches by tris(47-diphenyl-110-phenanthroline)rhodium(III),", *Biochemistry*, 1992, 31(24):5423-5429.

Deutsch, E. "Vitamin K in Medical Practice: Adults," 1966, *Vitam. Horm.*, 24:665-680.

Ennever et al, "Short Communication Photochemical Reactions of Riboflavin: Covalent Binding to DNA and to Poly (dA) Poly (dT)," 1983 *Pediatr. Res.* 17:234-236.

Friedman et al, "Reducing the Infectivity of Blood Components—What we have learned", 1995, *Immunological Investigations* 24 1&2: 49-71.

Ghiron et al, "The Flavin-sensitized Photoinactivation of Trypsin," 1965, *Photochemistry and Photobiology* 4:13-26.

Goodrich et al, "The design and development of selective, photoactivated drugs for sterilization of blood products," 1997, *Drugs of the Future*, 22(2):159-171.

Hanson, C.V., "Photochemical Inactivation of Viruses with Psoralens: An Orview", *Blood Cells*, 1992, 18:7-25.

Hanson, CV, "Photochemical Inactivation of Deoxyribonucleic and Ribonucleic Acid Viruses by Chlorpromazine", *Antimicrob. Agent Chemother.*, 1979, 15(3): 461-464.

Hoffmann et al, "DNA Strand Breaks in mammalian Cells Exposed to Light in the Presence of Riboflavin and Tryptophan", *Photochemistry and Photobiology*, 1979, 29:299-303.

Ivanchenko et al, "The photochemistry of purine components of nucleic acids. I. The efficiency of photolysis of adenine and guanine derivatives in aqueous solution,", 1974, *Nucleic Acids Res.* 2(8):1365-1373.

Joshi, P.C., "Comparison of the DNA-damaging property of photosensitized riboflavin via singlet oxygen (IO2) and superoxide radical (Oi) mechanisms," (1985) *Toxicology Letters* 26:211-217.

Kabuta, H. et al. (1978), "Inactivation of viruses by dyes and visible light," *Chem. Abstracts* 87(1), Abstract No. 400626.

Kale et al. (1992), "Assessment of the genotoxic potential of riboflavin and lumiflavin; B. Effect of light," *Mutation Res.* 298:17-23.

Klebanoff et al, "The Risk of Childhood Cancer after Neonatal Exposure ot Vitamin K," 1993, *New Eng. J. Med*, 329(13):905-908.

Kobayashi et al. (1983), "The molecular mechanism of mutation. Photodynamic action of flavins on the RNA-synthesizing system," *Chem. Abstracts* 98(1), Abstract No. 1200.

Korycka-Dahl et al, "Photodegradation of DNA with fluorescent light in the presence of riboflavin, and photoprotection by flavin triplet-state quenchers," (1980) *Biochimica et Biophysica Acta* 610:229-234.

Kovalsky et al, "Laser (Two-Quantum) Photolysis of Polynucleotides and Nucleoproteins: Quantitative Processing of Results," *Photochemistry and Photobiology*, 1990 5(6):659-665.

Kuratomi et al, "Studies on the Interactions Between DNA and Flavins", Biochemica et Biophysica Acta, 1977, 476:207-217.

Leontis et al, "The 5S rRNA loop E: Chemical probing and phylogenetic data versus crystal structure", *RNA*, 1998, 4:1134-1153.

Lim et al, "Chemical probing of tDNAPhewith transition metal complexes: a structural comparison of RNA and DNA", *Biochemistry*, 1993, 32:11029-11034.

Maddox, J., "The working of vitamin K," (1991) *Nature* 353(6346):695.

Malik et al, "New Trends in Photobiology—Bactericidal Effects of Photoactivated Porhyrins—an Alternative Approach to Antimicrobial Drugs," *J. Photochem. Photobiol* Pt.B: Biology, 1990, V:281-293.

Matthews et al., "Photodynamic therapy of viral contaminants with potential for blood banking applications," (1988) *Transfusion* 28(1):81-83.

McCord, EF, "Chemically induced dynamic nuclear polarization studies of yeast", 1984, *Biochemistry* 23:1935-1939.

Merenstein et al, (Vitamin K ad Hoc Task Force), "Controversies concerning vitamin K and the newborn," 1993, *Pediatrics* 901(5):1001-1005.

Merrifield et al, "Vitamin K as a fungistatic agent," 1965, *Appl. Microbio.* 13(5):660-662.

Merrifield et al, HY, "Factors affecting the antimicrobial acitivity of Vitamin K5," 1965, *Appl. Microbio.* 13(5):766-770.

Murata et al., "Effect of vitamins other than vitamin C on viruses: virus-inactivating activity of vitamin K5", *J. Nutr. Sci. Vitaminol*, 1983, Tokyo, 29(6):721-724.

Naseem et al., "Effect of alkylated and intercalated DNA on the generation of superoxide anion by riboflavin", *Bioscience Reports*, 1988, 8(5):485-492.

Neyndorff et al, "Development Of A Model To Demonstrate Photosensitizer-mediated Viral Inactivation in Blood," Quadra Logic Technologies, Inc., and the Department of Microbiology, U. of British Columbia 485-490 (Feb. 6, 1990).

North et al, "Photosensitizers as Virucidal Agents", *J. Photochem. Photobiol.*, 1993, 17(2), pp. 99-108.

North et al. (1993), "New Trends in Photobiology (Invited Review)," J. Photochem. Photobiol. B: Biol. 17:99-108.

Peak et al., "DNA Breakage Caused by 334-nm Ultraviolet Light is Enhanced by Naturally Occurring Nucleic Acid Components and Nucleotide Coenzymes", *Photochemistry and Photobiology*, 1984 39(5):713-716.

Piette et al., "Alteration of Guanine Residues During Proflavine Mediated Photosensitization of DNA", *Photochemistry and Photobiology*, 1981, 33:325-333.

Piette et al., "Production of Breaks in Single- and Double-Stranded Forms of Bacteriophage X174 DNA by Proflavine and Light Treatment", *Photochemistry and Photobiology*, 1979, 30:369-378.

Pratt et al, "Vitamin K5 as an Antimicrobial Medicament and Preseravative", *J. Am. Pharm. Assn*, 1959 39(3):127-134.

Reinhardt et al, "Virucidal activity of retinal," *Antimicrobial Agents and Chemotherapy*, 1979, 16(3):421-423.

Shwartzman, G., "Antibacterial Properties of 4-Amino-2-Methyl-1-Naphthol Hydrochloride," 1948, *Proc. Soc. Exp. Biol. Med.* 67:376-378.

Simukova et al, "Conversion of Non-covalent Interactions in Nucleoproteins into Covalent Bonds: UV-Induced Formation of Polynucleotide-Protein Crosslinks in Bacteriophage Sd Virions," 1974, *FEVS Letters* 38(3):299-303.

Speck et al., "Further Observations on the Photooxidation of DNA in the Presence of Riboflavin," *Biochimica et Biphysica Acta*, 1976, 435:39-44.

Spranger, J. "Does vitamin K cause cancer?" 1993, *Eur. J. Pediatr.* 152(2):174.

Tsugita et al., "Photosensitized inactivation of ribonucleic acids in the presence of riboflavin", *Biochim. Biophys. Acta*, 1965, 103:360-363.

Uehara et al, "Effect of ademine on the riboflavin-sensitized photoreaction. II. Effect of adenine on the photodynamic inactivation of transforming deoxyribonucleic acid in the presence of riboflavin", 1972, J Biochemistry, 71:5, 805-810.

Uehara et al, "Effect of adenine on the riboflavin-sensitized photoreaction. I. Effect of adenine on the photodynamic inactivation of yeast alcohol dehydrogenase in the presence of riboflavin", *J. Vitaminology*, 17:3,1971,148-154.

Vest, M., "Vitamin K in medical practice; pediatrics," 1966, *Vitami. Horm.* 24:649-663.

Way et al, "HPLC Analysis of Riboflavin and its Photodegradation products in an Intravenous Infusions Formulation", 1990, Pharm Res., 7(9). Suppl., S26, in DRGU, aN 1991-11544.

Webb et al, "Mutagenesis in *Escherichia coli* by Visible Light", *Science*, 1967, 156:1104-1105.

Yang et al, "Vitamin K5 as a Food Preservative", *Food Technology*, 1958, 501-504.

\* cited by examiner

USE OF VISIBLE LIGHT AT WAVELENGTHS OF 500 TO 550 NM TO REDUCE THE NUMBER OF PATHOGENS IN BLOOD AND BLOOD COMPONENTS

PRIORITY CLAIM

This application is a Continuation-In-Part of U.S. patent application Ser. No. 10/377,524, filed Feb. 28, 2003, which is a continuation of U.S. patent application Ser. No. 09/586,147, filed Jun. 2, 2000, now abandoned, which is a Continuation-In-Part of U.S. patent application Ser. No. 09/357,188, filed Jul. 20, 1999, now U.S. Pat. No. 6,277,337, which is a Continuation-In-Part of Ser. No. 09/119,666 filed Jul. 21, 1998, now U.S. Pat. No. 6,258,577. This application also claims the benefit of U.S. Provisional No. 60/580,311, filed Jun. 15, 2004.

BACKGROUND

As pointed out by the NIH (National Institutes of Health) in a recent RFA (Request for Applications) "3.8 million Americans are transfused with 28.2 million blood components derived from 12.8 million units of blood donated by apparently healthy volunteers." Blood products are extensively tested for the presence of pathogens prior to administration in the developed world. Nevertheless, there exists a small, but finite risk of transmission of infectious agents in a transfusion. In its RFA, the NIH estimated the risk during transfusion "of a unit of screened blood is 1/1,000,000 for hepatitis A virus (HAV), is 1/30,000-1/50,000 for hepatitis B (HBV), 1/30,000-1/150,000 for hepatitis C (HCV), 1/20,000-1/2,000,000 for human immunodeficiency virus (HIV), 1/250,000-1/2,000,000 for human T-cell lymphotropic viruses (HTLV) types I and II and 1/10,000 for parvo virus B1. Furthermore, the estimated frequency of bacterial contamination of red blood cells is 1/500,000 units and the risk of platelet-related sepsis is estimated to be 1/12,000" as of the year 2000.

The risks of viral infection are due to the "window period," the period of time between the infection of a donor and the development of detectable levels of antibodies. The introduction of nucleic acid testing (NAT) has shortened the window period and further decreased the incidence of units of blood products containing pathogens. NAT was introduced for HIV and HCV in the United States in 1998. This new technology has greatly reduced the risk as the window period has been dramatically decreased. The window period for HIV was reduced from 22 days to 11 days and the window period for HCV has been reduced from 70 days to 8-10 days. This new technology has brought the risks per unit of donated blood to 1:1,800,000 for HIV and 1:1,600,000 for HCV. When these statistics are compared to the current risk of 1:220,000 associated with HVB, a virus for which NAT is not currently performed, the need for additional pathogen reduction technologies is apparent. As the blood supply in the developed world is relatively safe, any technology that further decreases the incidence of pathogens in blood products must itself be incredibly safe to be of net benefit to public health.

Sadly, blood products are still not screened prior to administration in many parts of the world. In underdeveloped countries, the cost of introducing testing protocols exceeds the local resources. The blood supply in too many countries tragically contains high levels of pathogens, especially parasitic organisms such as those responsible for Chagas Disease and Malaria. New technology which can improve the safety of the blood supply in underdeveloped portions of the globe must be simple and inexpensive if it is to receive widespread use.

A simple technology which has been used to sterilize at least some portions of the blood such as plasma is UV light. However, pathogens are composed of the same amino acid, nucleic acid, and lipid building blocks as plasma proteins, platelets, and red cells. Consequently, there is no known wavelength of light which can be selectively deposited into pathogens in the presence of blood products. Pathogens, plasma proteins, and platelets absorb UVB (280-320 nm) and UVC (200-280 nm) radiation. This inactivates pathogens, but with unacceptable damage to plasma proteins and platelets. Red cells absorb this type of radiation so strongly that one cannot inactivate pathogens with UVB and UVC radiation in their presence. UVA radiation (320-400 nm) alone does not inactivate a virus. It does, however, shorten the shelf life of platelets.

This fact has led practitioners to study sensitizers. By definition, sensitizers absorb light and initiate chemical reactions that inactivate pathogens. Thus, it is no surprise that sensitizers themselves undergo chemical change upon photolysis. Therefore, not only must the ideal sensitizer be innocuous, but every molecule it degrades to upon photolysis must be non-toxic and non-mutagenic as well.

Ideally, a sensitizer will absorb long wavelength light ($\lambda$>400 nm) that is not absorbed by plasma proteins or platelets. If the sensitizer binds only to pathogen, in the presence of plasma protein and platelets, radiant energy in the UVA or visible region of the spectrum can be deposited selectively into the pathogen, even in the presence of blood components. This can lead to inactivation of the pathogen, in principle, by various chemical reaction mechanisms.

In the absence of pathogen, the ideal sensitizer will not bind to transfusable blood product. Thus the ideal sensitizer must recognize and exploit a chemical difference between the pathogen and the blood product. There is a chemical difference between many pathogens and plasma proteins. Bacteria and many types of virus are encapsulated by phospholipid membranes or envelopes, but plasma proteins are not. Pooled plasma is treated with solvent detergent that dissolves membranes and inactivates many types of pathogens without damage to the plasma protein. Recently, Cerus Corporation has developed a technology for pathogen reduction of platelets that has been approved for use in Europe. At this time there is no pathogen eradication technology used to treat red cells before their administration in transfusion medicine, anywhere in the world.

A successful photochemical technology that will eradicate pathogens present in blood products requires that the perfect sensitizer has the following properties: the ideal sensitizer must bind to pathogenic particles but must not bind to plasma proteins, platelets or red blood cells. Secondly, the ideal sensitizer should be non-toxic, non-mutagenic and must not break down to compounds that are toxic and mutagenic. It should be readily available, water soluble, and inexpensive. Finally, the ideal sensitizer must absorb UV and/or visible radiation. Absorption of radiation must produce a short-lived, highly-reactive toxin, which creates lesions in its immediate vicinity (e.g., only to the pathogenic particle to which it is bound).

Molecules that are currently under investigation, which fulfill many of the above-mentioned requirements, have flavin moieties and are members of the alloxazine family, in particular, riboflavin.

BRIEF SUMMARY OF THE INVENTION

This invention is directed towards a process for substantially preventing damage to blood components in a fluid which contains pathogens having nucleic acids. The process includes adding to the fluid a sensitizer having a flavin moiety; letting the sensitizer bind to the nucleic acids of the pathogens; irradiating the fluid and sensitizer with light at a wavelength between 500-550 nm to activate the sensitizer which is bound to the nucleic acid of the pathogen; and inactivating the pathogen.

DETAILED DESCRIPTION

Figure 1A:
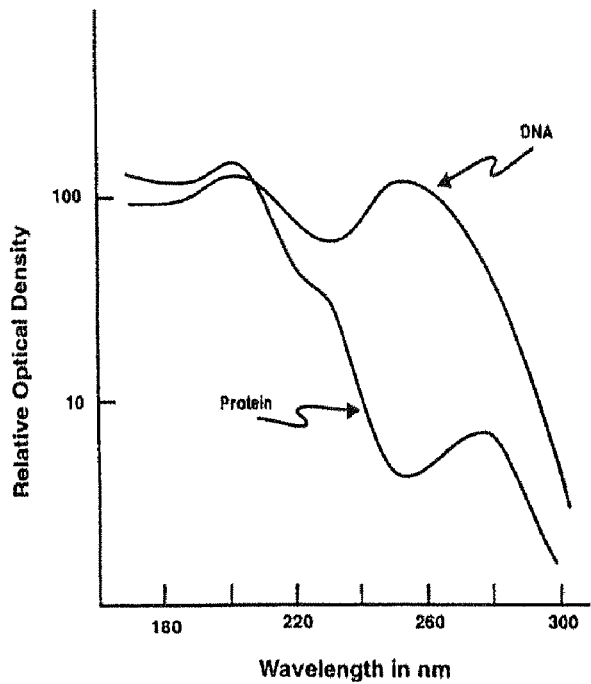
FIG. 1 shows the absorption curves of nucleic acid and protein.

Riboflavin (RB, vitamin $B_2$) is a vitamin essential to the human diet. It is present in aerobic organisms and is found in many foodstuffs such as milk, beer, eggs, yeast and leafy vegetables. It is also the precursor for flavin mononucleotide (FMN) and flavin adenine dinucleotide (FAD), which are major coenzymes that participate in a number of one-electron processes in the human body.

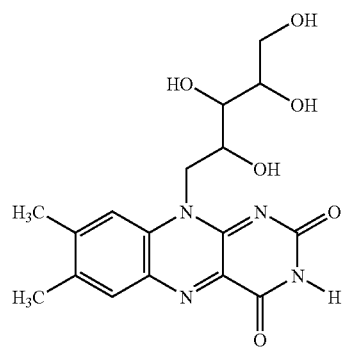

Riboflavin has absorption maxima at 220, 265, 375, and 446 nm in water and is yellow-orange in color. When aqueous solutions containing riboflavin are exposed to sunlight, riboflavin is converted into lumichrome (LC) under neutral conditions, and into lumiflavin (LF) in alkaline solutions. LC is also a known metabolic breakdown product of riboflavin in the human body.

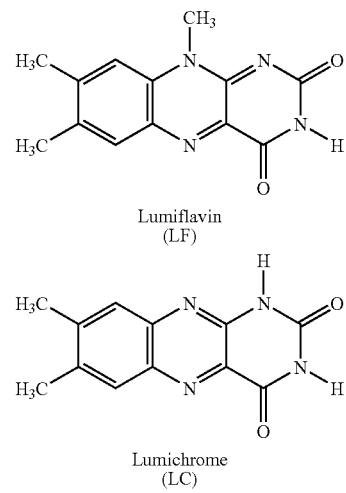

Lumiflavin (LF)

Lumichrome (LC)

Flavin systems are known to be photochemically active, and products of flavin photochemistry are known to react with a host of biological molecules, often with clinical implications.

Advantages of using riboflavin as a sensitizer include the fact that riboflavin is "Generally Regarded As Safe" or GRAS by the FDA. Its photochemical breakdown products (lumichrome and lumiflavin) are metabolites of riboflavin and thus are formed naturally in vivo. Inadvertent riboflavin photolysis takes place in the blood of neonates treated for hyperbilirubinemia. In vivo riboflavin photochemistry does not lead to an incidence of cancer in treated neonates. Secondly, riboflavin can be activated with visible light that is not absorbed strongly by plasma or platelets. Thirdly, platelets treated with riboflavin and light, under conditions which inactivate high titers of pathogen, circulate normally when reinfused into autologous hosts.

Thus, technology based on an endogenous sensitizer like riboflavin is much more likely to be both efficacious and safe than technology based on a synthetic sensitizer (e.g. a psoralen or methylene blue). Riboflavin also has the advantage over other possible synthetic photosensitizers because it is a naturally occurring, essential vitamin-with no known toxicity.

Use of riboflavin as a sensitizer in a pathogen reduction procedure to pathogen reduce blood and blood components has been disclosed in U.S. Pat. Nos. 6,258,577 and 6,277,337.

Riboflavin Photophysics and General Photochemistry

Sensitizer photophysics and photochemistry of riboflavin, can be usefully summarized with the aid of the Jablonski diagram below. The sensitizer in its ground electronic state is referred to as $S_0$. Upon absorption of light, the sensitizer is converted to an electronically excited state that, in the condensed phase, immediately ($<<10^{-11}{}_s$) relaxes to the lowest vibrational level of the lowest excited state ($S_1$). The lifetimes of $S_1$ states in solution are usually in the range of 0.1-10 ns and are controlled by internal conversion (IC) and fluorescence (F) decay back to $S_0$, by intersystem crossing (ISC) to a paramagnetic triplet state ($T_1$) and by inter- and intramolecular chemical reactions. Because $S_1$ is short-lived, bimolecular reactions of $S_1$ will be inefficient unless the trapping agent is rather concentrated (0.1-1.0 M) or the sensitizer and the trap are complexed. A sensitizer bound to protein or nucleic acid will likely react in its $S_1$ state. Common reactions of $S_1$ are electron transfer and cycloaddition. Fluorescence quenching is characteristic of bimolecular reactions of $S_1$.

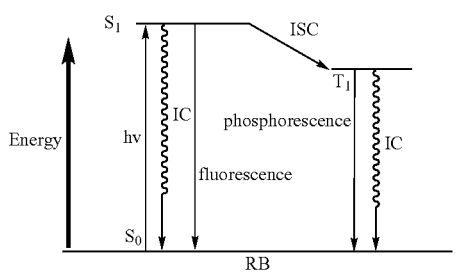

Sensitizer triplet states are much longer lived than excited singlet states. Their lifetimes are typically controlled by bimolecular reactions, particularly reaction with oxygen, a molecule with a triplet ground state. This reaction often leads to the formation of singlet oxygen, a potent oxidizing agent that is employed in many lipid-targeted, photosensitized, viral inactivation strategies.

The generally accepted major photochemical processes available to riboflavin (RB) in the presence of a suitable substrate (R—H), such as electron-rich amino acids (e.g. tryptophan and tyrosine) or guanosine, are shown below.

gen-atom donors. It has also been hypothesized that $^3RB^*$ may abstract a hydrogen-atom directly from a substrate, such as when R—H=sugar, (dashed arrow) without the intermediate electron and proton-transfer steps.

Riboflavin Photochemistry as a Sensitizer

Nucleic Acid Targeted Sensitizers

All potential pathogens present in the blood supply (with the possible exception of prions) contain genomic nucleic acids. Viruses may be either RNA or DNA based, single or double stranded, enveloped or non-enveloped, but all contain nucleic acids. Genomic nucleic acids have the specific purpose to propagate the organism or cellular population in which it is located. Plasma proteins, platelets, and red cells do not contain genomic nucleic acids. Plasma proteins are composed of amino acids and do not contain nucleic acids. Platelets are generated from other blood cells but they themselves do not reproduce. Platelets do have mitochondrial DNA, but do not possess genomic DNA. Human red cells have no nucleus and do not contain any nucleic acid.

To a crude, first approximation, any genomic nucleic acid present in a unit of donated blood is undesirable. The only genomic nucleic acid material in a unit of blood products would be due to either bacterial or viral pathogens. A sensitizer, which binds nucleic acids but does not bind to phospholipids or proteins, might be able to exploit this chemical difference and selectively inactivate virus and bacteria in the presence of plasma protein, platelets, and red cells. Therefore, technology that can damage the nucleic acid framework while

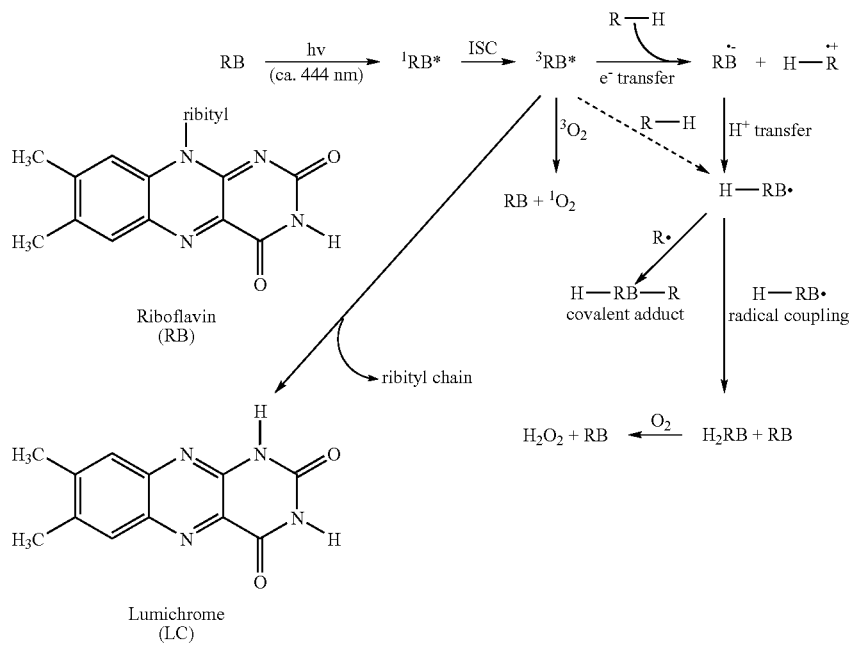

The first step in the photochemistry of RB is the excitation of the singlet ground state ($S_0$) to the singlet excited state ($^1RB^*$, $S_1$). The singlet excited state can fluoresce ($\phi_F$=0.26, $\tau_F$=5 ns, 520 nm), or undergo rapid intersystem crossing, ISC, ($\phi_{ISC}$=0.7) to the triplet excited state ($^3RB^*$, $T_1$, $\tau_{T_1}$=10-100 μs). The triplet flavin can phosphoresce ($\phi_P$=0.0012, $\tau_P$=0.1-0.2 s, 610 nm) or undergo further chemistry, which is dictated by the availability of oxygen, and suitable electron and hydroleaving the remaining blood components untouched will be a useful method for sterilizing blood and blood components.

As discussed above, UV radiation damages DNA, but it also damages many other biological compounds as well. If a compound can bind DNA, and upon activation, cause enough damage such as nicks and cross-links, then the DNA cannot be repaired and replicated. Riboflavin is known to bind weakly to nucleic acid. It has been shown by Dardare et. al that riboflavin has little affinity for albumin and for phospholipids, but it does have a small but finite binding affinity for calf thymus DNA. From Scatchard plots, Kuratomi and Kobayashi have deduced that one flavin or alloxazine molecule is bound to every 500 nucleotides of native nucleic acids. Since riboflavin appears to selectively bind DNA, and since riboflavin can be photo-excited with low energy visible light, which is expected to be more selective with respect to undesired photolytic damage of the DNA bases themselves, riboflavin is under study as a sensitizer of nucleic acid damage in the presence of other biological chromophores. One possible site of riboflavin sensitized DNA damage is in the sugar backbone of the helix and the electron-rich guanosine residues.

Riboflavin sensitized photolysis of DNA produces 8-oxoguanosine and single strand breaks in addition to adducts of flavin and nucleic acid. Cadet and coworkers have shown that excited riboflavin can accept an electron from guanosine to form the guanosine radical cation. Subsequent hydrolysis of the guanosine radical cation also produces 8-oxoguanosine. Thus 8-oxoguanosine can be formed by more then one mechanism and at least by one mechanism without the intervention of singlet oxygen, hydrogen peroxide or superoxide ion.

Yamamoto, Nishimura and Kasai have analyzed the DNA of cultured mammalian cells (mouse lymphoma line L5178Y) exposed to riboflavin and visible light and found that 8-oxoguanosine was produced. Previously, Hoffman and Meneghini discovered that photolysis of green monkey kidney cells and riboflavin led to the formation of single strand breaks of the cellular DNA. Thus, it is a straightforward conclusion that photolysis of intracellular riboflavin produces intracellular oxidants that damage cellular DNA and/or that photolysis of extracellular riboflavin generates extracellular hydrogen peroxide that can passively transport to the cell nucleus and damage the cellular DNA. There seems little doubt that this is the mechanism for much cellular DNA damage but Cadet's work indicates that it is probably not the only intracellular riboflavin sensitized photochemistry which transpires. Furthermore, Ennever and Speck have demonstrated the flavin-nucleic acid adducts are formed when riboflavin and nucleic acids are exposed to visible light. The formation of these adducts is not oxygen dependent.

Photolysis of RB

It is well known that long-lived oxidants such as hydrogen peroxide and superoxide anion are produced when riboflavin in water or growth medium is exposed to visible light. These effects are enhanced in the presence of electron donors such as tryptophan and tyrosine. Short-lived oxidants such as singlet oxygen are also formed upon photolysis of riboflavin.

The first step in the formation of long lived oxidants involves electron transfer from a donor (tryptophan, tyrosine, ground state flavin) to either the excited singlet or triplet state of riboflavin to form the flavin radical anion (RB·). The reaction scheme for the formation of superoxide from riboflavin (RB) is shown below.

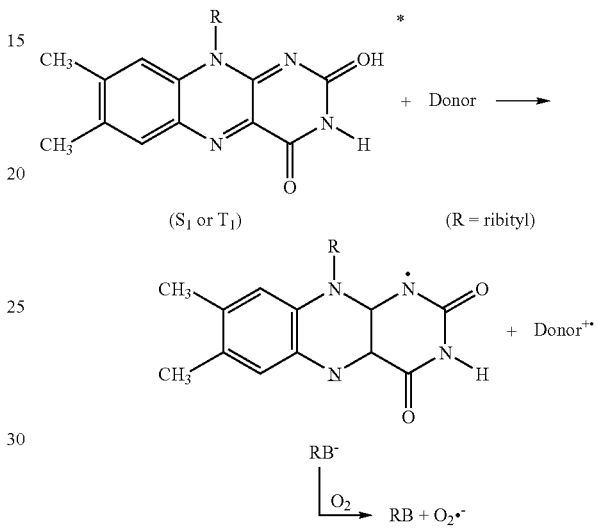

There are many plausible mechanisms by which reactive oxygen species (ROS) can be formed from the radical anion of the flavin. An electron can be transferred from the radical anion of riboflavin to oxygen to form superoxide anion. Alternatively, protonation of the reduced flavin forms a neutral radical RBH· which can react with oxygen to form a hydroperoxy radical (RBOO·). The reaction pathway for the formation of hydrogen peroxide ($H_2O_2$) from irradiated riboflavin (RB) is shown below.

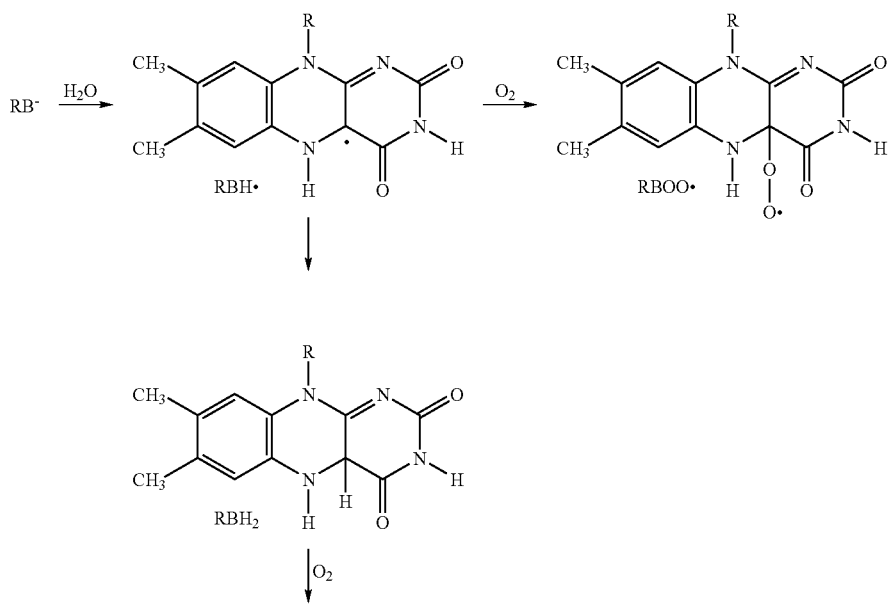

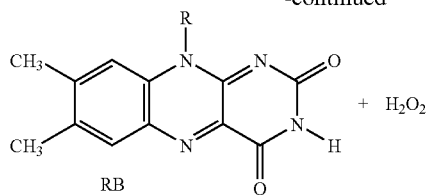
-continued

Complete reduction of riboflavin forms leukoflavin, $RBH_2$. This species is stable in solution in the absence of oxygen. However, it reacts very rapidly with oxygen to form hydrogen peroxide and to regenerate riboflavin. In this manner the photochemical formation of hydrogen peroxide can be catalytic rather than stoichiometric in riboflavin. The simplicity of the overall reaction of leukoflavin with oxygen is deceptive. The overall reaction is actually a multistep sequence involving superoxide ion.

Hydrogen peroxide and superoxide ion both react with guanosine residues of cellular DNA. Isolation and digestion of the cellular DNA yields either 8-oxoguanosine or 8-oxoguanine depending on the methodology employed to digest the nucleic acid.

Hydrogen peroxide also induces single strand breaks when added to nucleic acids, and is toxic to cells.

Action Spectra of Riboflavin

Action spectroscopy is a general approach used to identify the species containing the chromophore that is responsible for a specific photochemical or photobiological reaction. The most basic action spectrum consists of a plot of a specific response as a function of wavelength at a constant dose of irradiation (fluence), usually in terms of joules per square meter ($J/m^2$). The "specific response" against which the irradiating wavelength is plotted against could be a wide variety of measurements ranging from lethality and viability to growth and induced mutation and even chemical yields and product ratios.

Figure 1B:
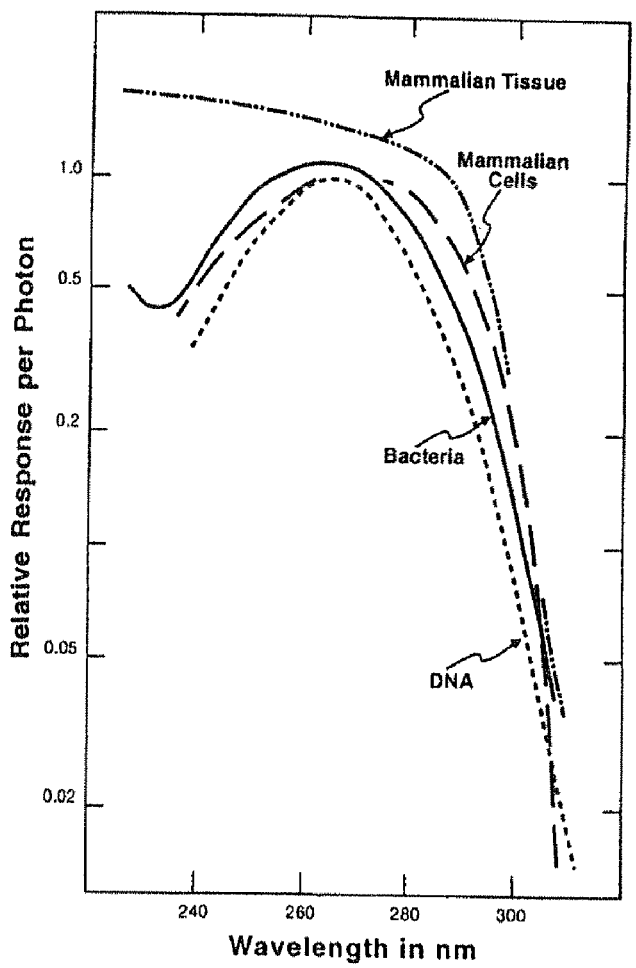

The absorption curves for nucleic acid and protein is shown in FIG. 1a. FIG. 1a shows the UV absorption curves of DNA and bovine serum albumin (1% and 1 cm path length). FIG. 1b shows the UV action spectra for killing bacteria, mammalian cells and mammalian tissue. Note that the shape of the action spectrum is the same for both kill and UV absorption by DNA.

Ideally, an action spectrum should have the following characteristics.
1. The quantum yield for the event responsible for the desired effect should be wavelength independent.
2. The absorption spectrum of the chromophore should be the same in vivo and in vitro.
3. Screening chromophores (not contributing to the specific measured response) should not cause a wavelength-specific distortion. The same is true for light scattering.
4. Action spectra derived from fluence-response curves should be dependent on the product of the fluence rate ($J \cdot m^{-2} s^{-1}$) and the exposure time (s), but not depend specifically on either one. (Condition of Reciprocity)
5. The light should not be completely absorbed by the sample. Some guidelines suggest that the sample should not absorb any more than 50% of the light at the wavelength under investigation. (Absorption=0.30)

EXAMPLES

Systems used to study pathogen inactivation often include the study of bacterial viruses or phages, which are easy to handle, provide rapid results, are safer than working with human pathogens, and are available with a wide range of biological variation. For example, many studies aimed at understanding HIV (Human Immunodeficiency Virus) have been performed using the feline variant (FIV) or simian variant (SIV).

Lambda phage is a bacteriophage that has *Escherichia coli* as its host. Lambda phage contains double-stranded DNA that is loosely encapsulated within a protein sheath. Approximately 50,000 DNA base pairs account for about 50% of the total lambda phage mass, the rest of which arises from protein. Lambda phage enters into the host via the receptor that transports maltose the cell. Once inside the host, the phage can reproduce.

One method for determining the titer of viable phage is by a plaque assay. Lambda phage plaque assays have been used in a wide variety of scientific investigations, including those involving the genotoxicity of illuminated riboflavin and viral inactivation from photosensitizers that bind DNA.

In a plaque assay, a sample containing the phage in question is diluted serially (10-fold) and each resulting solution is incubated in an excess of the bacterial host. This phage-host mixture is then plated out in agar with the appropriate growth media and the bacteria are permitted to propagate under favorable growth conditions specific for the bacteria.

When an individual host cell is infected, the phage propagates and the host undergoes lysis. The ruptured host then releases its cellular contents and the propagated phage into the agar matrix, which then infects neighboring bacteria. This cycle continues until a "plaque" is formed, which is a small circular region devoid of bacterial growth in the bacterial lawn on the agar support. In this way, one can count the number of plaques on an agar plate originating from a solution with a known dilution factor. The starting titer of phage can then be calculated from the collected data. By comparing the titer of a sample before and after a specific treatment, the amount of phage inactivation can be determined.

Using the methods described above, an action spectrum of the riboflavin-sensitized inactivation of lambda phage may answer several interesting and useful questions.
1. Is there an irradiation wavelength that gives a maximal amount of viral inactivation while producing a minimal amount of damage to desired blood products?
2. Will the action spectra follow the absorption profile of aqueous riboflavin? If not, does it resemble the absorption profile of a photoproduct or a flavin bound to a bio-macromolecule?
3. What role (if any) do the photoproducts and ROS play in the viral inactivation as a function of wavelength?

Example 1

Figure 2:
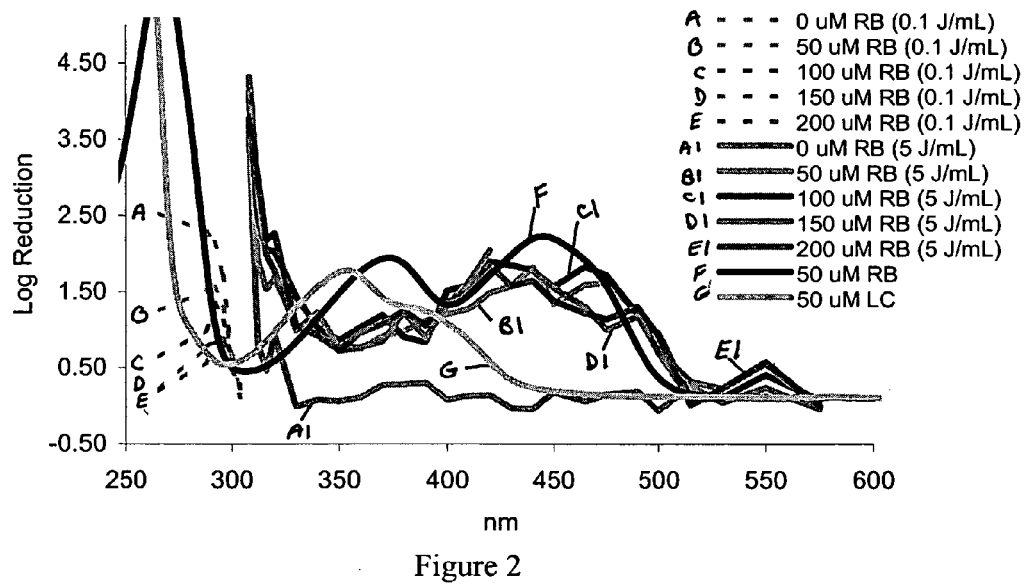
FIG. 2 shows the action spectra of the inactivation of lambda phage in PBS at 0.1 J/mL.

The action spectra of the inactivation of lambda phage in phosphate buffered saline (PBS) with 0, 50, 100, 150 and 200 µM riboflavin was determined between 266-575 nm. Each irradiated sample is based on 2.5 mL of solution in a 3.0 mL quartz cuvette. Each data point was performed in triplicate and the reported value reflects the average of these three values. As shown in FIG. 2, the action spectra can be divided up into two distinct regions based on the energy required for inactivation, and the effect of the sensitizer.

Action Spectra: 266-304 nm

It has been known for many years that UV radiation with wavelengths of less than or equal to 304 nm is lethal to cells. However, the effect of the addition of the photosensitizer riboflavin, on the action spectrum in this region was not known. As can be seen in FIG. 2, the action spectra for the inactivation of lambda phage in PBS from 266-304 nm requires only 0.1 J/mL to achieve a maximum phage reduction of 2.5 logs in this region. As the action spectrum approaches 304 nm, the reduction of phage drops off sharply as the absorption curve of DNA also approaches zero.

As shown in FIG. 2, phage inactivation is dominated by direct light absorption by the phage from 266-304 nm. Not only does the presence of riboflavin fail to increase the extent of phage inactivation, but the presence of riboflavin also reduces the amount of phage inactivation by acting as a screening agent that decreases the amount of light that is absorbed by the phage. This screening effect is proportional to the concentration of riboflavin in solution. Since the competitive absorption of riboflavin dominates any sensitization of the phage, it is concluded that direct absorption of light by the phage is much more efficient at phage inactivation compared to sensitized inactivation.

Although the quantity of phage inactivation decreases with increasing riboflavin concentration when the sample is irradiated between 266-304 nm, this does not necessarily mean that riboflavin is acting only as a screening agent. One concern that exists when considering methods of pathogen inactivation is the possibility of host re-activation. Basically, defense and repair mechanisms (within bacteria and existing in hosts for viruses) have the ability to repair DNA damage and reverse pathogen inactivation. In systems that have undergone a specific type of stress that leads to damage (i.e. peroxides), particular repair mechanisms may be stimulated and be activated to repair this type of damage to the pathogens. The result is less-than-expected pathogen inactivation. Therefore, it would be beneficial to control the type of damage that is responsible for pathogen inactivation to a type that is more difficult to repair. As a result, the DNA damage would not be as efficiently repaired and the viral titer would remain low instead of rebounding due to DNA repair.

When DNA is irradiated with UV light, most of the damage consists of thymine-thymine dimers (T<>T). In terms of quantum yield, the majority of the energy of photoexcited DNA is lost to the system in the form of heat rather than chemical change. In the presence of riboflavin, the photochemistry of DNA could then follow a different pathway. If light that is absorbed by DNA results in a guanosine excited-state singlet, $*G^1$, which then relaxes to the excited-state triplet, $*G^3$, then an electron transfer can occur from guanosine to riboflavin. Alternatively, triplet thymine could undergo an energy transfer to riboflavin, which could then react with an electron donor such as guanosine. The guanosine radical cation can then be oxidized by water to form 8-oxo-guanosine, which is a lesion that is less easily repaired. Therefore, there may be a benefit from riboflavin in the inactivation of lambda phage from 266-304 nm that is manifest as a more lethal DNA lesion that is not as easily repaired by host reactivation.

Action Spectra: 308-575 nm

To achieve the same magnitude of log reduction that was observed between 266-304 nm, the energy required for the experiments between 308-575 nm was increased 50-fold from 0.1 J/mL to 5.0 J/mL.

Figure 3:
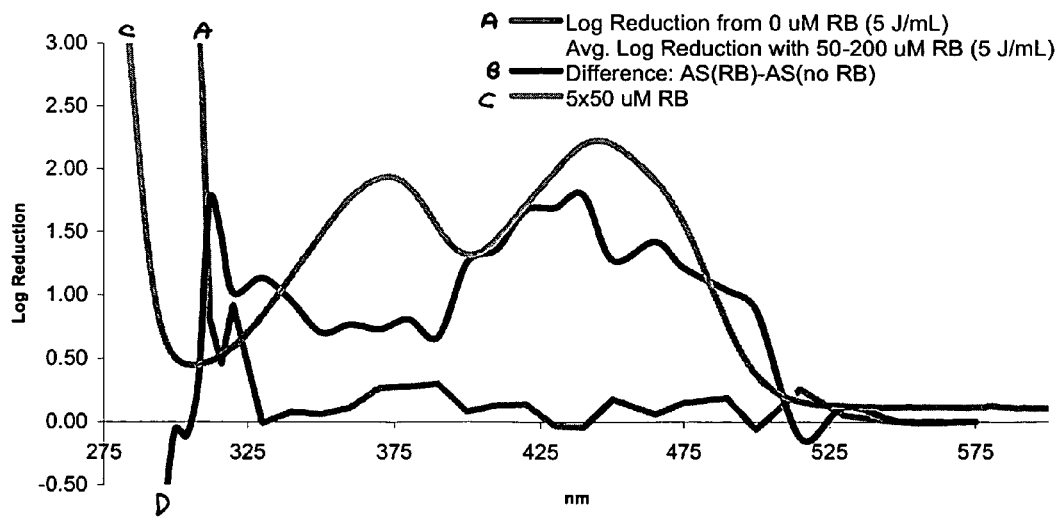
FIG. 3 shows the action spectra of the inactivation of lambda phage in PBS at 5 J/mL.

This action spectra is shown in FIG. 3. The action spectra was measured for samples containing either no riboflavin (no RB), or for the average inactivation due to 50-200 μM riboflavin (RB). The net effect (shown in the legend as difference) from the addition of riboflavin (RB sensitized—unsensitized) on the action spectrum (AS) and the absorption curve of riboflavin is also shown.

The action spectra do not correlate perfectly with the absorption curve of either riboflavin or lumichrome over the entire wavelength regime. There appears to be essentially an identical amount of viral inactivation at 355 and 500 nm, although the optical densities (of solutions containing the same concentration of riboflavin) differ by a factor of five at these wavelengths. There also appears to be a large amount of inactivation at 320 nm, which was contrary to expectations, as riboflavin in water does not have an absorption maximum in this region. The inactivation at about 500 nm is slightly higher than expected compared to the absorption curve of riboflavin and the inactivation at 375 nm where riboflavin absorbs is lower than expected. Additionally, the region between 308 nm (the point at which the riboflavin switches from screening direct absorption of light by the phage to sensitized inactivation) and 350 nm appears to have more riboflavin sensitized inactivation than expected based upon the absorption curve of riboflavin.

An area where the inactivation in the presence of riboflavin is larger than expected is at 500 nm. Since there is no inactivation at this wavelength in the absence of sensitizer, the value added of riboflavin is very clear.

Example 2

When the log reduction of phage is 0.5 logs or lower, concern exists that the magnitude error bars of the assay are approaching that of the data itself. Since the area in the action spectrum around 500 nm is of interest, a closer examination was performed in this region. Therefore, the action spectrum points were redone at 500, 510, 530, 550, and 575 nm with 0, 50, 100, 150, and 200 uM riboflavin and with 25 J/mL of delivered laser radiation. When these results are examined, an interesting feature begins to emerge.

Figure 4:
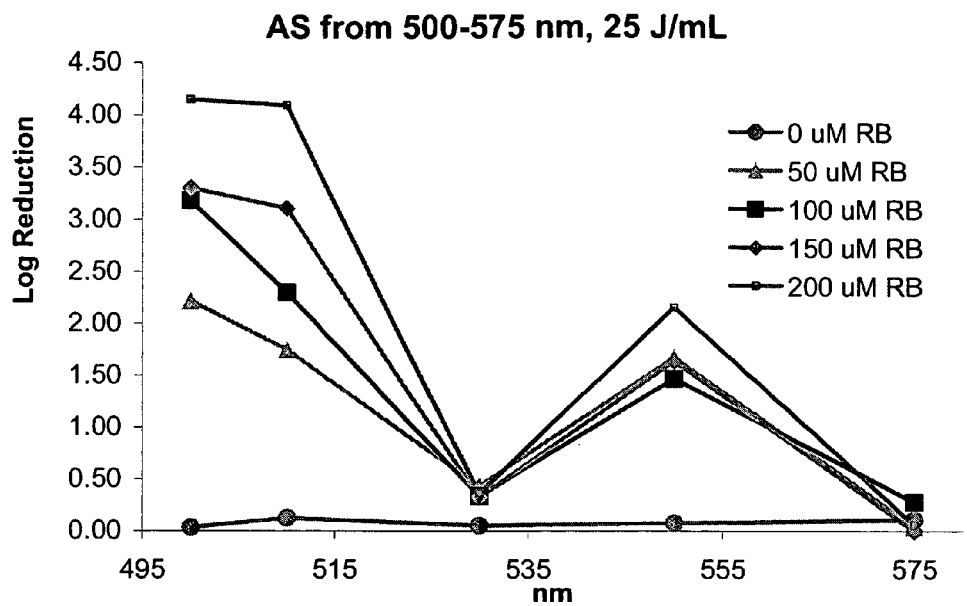
FIG. 4 shows the action spectra of the log reduction of lambda phage in PBS at 25 J/mL at 500-575 nm.

FIG. 4 shows the log reduction of lambda phage in PBS containing 0, 50, 100, 150, and 200 uM riboflavin (RB) after receiving 25 J/mL at 500 nm.

Examination of the data obtained after exposure to 25 J/mL between 500-575 nm reveals that there may be an additional inactivation maxima at 550 nm.

Figure 5:
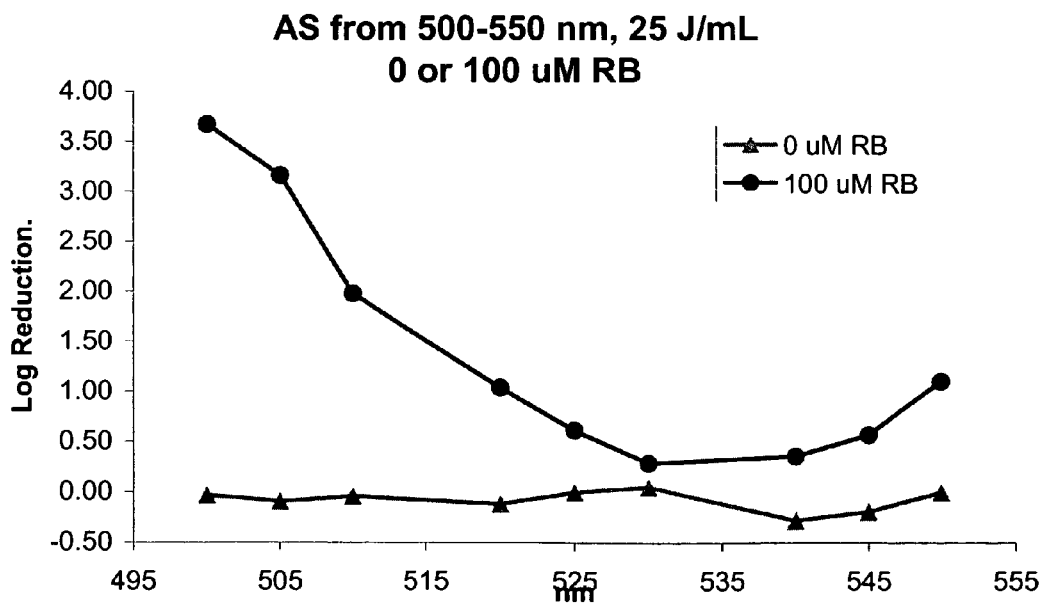
FIG. 5 shows the action spectra of the log reduction of lambda phage in PBS at 25 J/mL at 500-550 nm.

Since this action spectra now strongly suggests that there is another region of significant viral inactivation well beyond the absorption curve of aqueous riboflavin, the action spectra from 500-550 nm (FIG. 4) was repeated with much smaller steps of 5-10 nm between individual irradiation wavelengths. The experiment was performed using only 100 uM riboflavin as the sensitizer and 25 J/mL of laser radiation at the designated wavelength. The results are shown in FIG. 5, which shows the log reduction of lambda phage in PBS containing 0 or 100 μM RB after receiving 25 J/mL. (all data N=1)

The data suggests that there may be a new region of increased viral inactivation in the region between 500-520 nm and possibly at 550 nm.

Example 3

Binding of Flavins

Any riboflavin that is bound to phage in the action spectra studies is in such minute concentrations that a UV-visible shift due to bound flavin is impossible to obtain, although the effect of bound flavin could dominate the action spectra.

Therefore any shifts in the UV-visible absorption spectra due to flavin binding to several biological macromolecules was studied.

A route to study the possible shift in absorption spectra due to riboflavin binding includes the study of aptamer binding. Aptamers are specific sequences of RNA that have a high binding affinity for a specific substrate. Several literature reports indicate that an aptamer that tightly binds FMN may be a suitable model to study absorption spectra shifts upon riboflavin binding. As mentioned above, FMN is the phosphorylated form of riboflavin. FMN is more water soluble then riboflavin, but the flavin moiety is identical to that of riboflavin. It can be extrapolated from the below data that riboflavin would behave identically to FMN. The aptamer sequence (GGC GUG UAG GAU AUG CUU CGG CAG AAG GAC ACG CC) was custom synthesized, purified, and deprotected and was used as received. The aptamer was prepared in RNAse free buffer PBS (autoclaved with 0.1% diethyl pyrocarbonate [DEPC]) containing 0.1 mM EDTA and 4 mM $Mg^{+2}$. The magnesium was reported to be critical for proper folding of the aptamer and consequent binding of the flavin ring of FMN.

Figure 6:
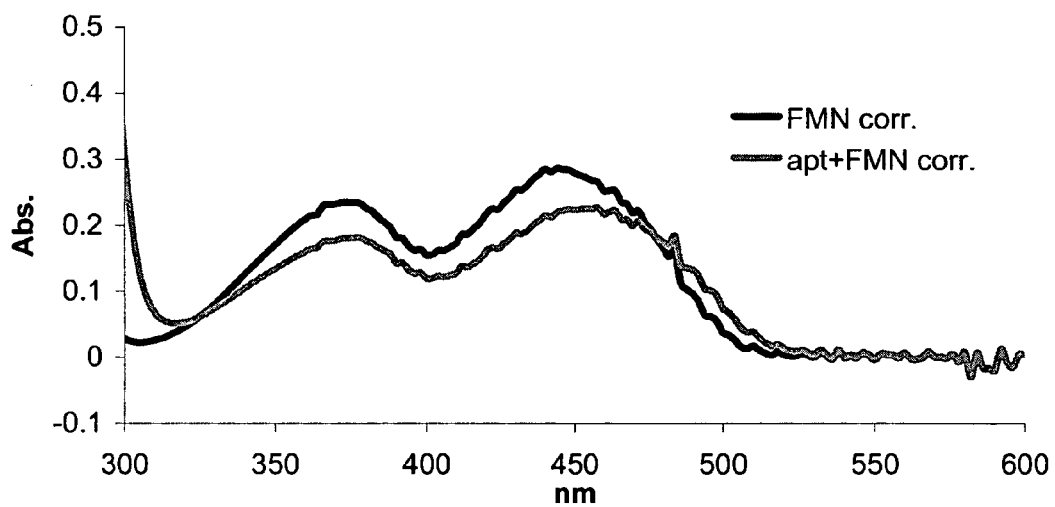
FIG. 6 shows the absorption spectrum of 200 µM aptamer compared to aptamer+FMN.

The difference spectra were obtained with both 100 and 200 μM each RNA aptamer and FMN. Only the data for the 200 μM concentrations are shown in FIG. 6, which shows the absorption spectrum of 200 μM FMN and shifted spectrum due to 200 μM aptamer [path length=0.1 cm].

The negative values in the difference spectrum (ca. 370 and 445 nm) are due to the lower molar absorptivity of the bound flavin compared to the free flavin. If one could obtain a spectrum of pure aptamer-bound FMN, the result would be an absorption spectrum with an absorbance greater than or equal to zero at all points (i.e. no subtraction error). One can express the final concentration of the species after binding by the following equation, where $\chi$ is the concentration of the FMN-aptamer complex at equilibrium.

flavin bound to nucleic acids since this is the first instance that all of the absorbance values are greater than zero.

Example 4

If the flavin is bound within the phage, the flavin absorption spectrum may shift due to the differing dielectric constant of the binding region. To probe this area, the absorption spectrum of an aqueous solution of riboflavin was compared to a solution (with the same riboflavin concentration) containing different ratios of other solvents in an attempt to observe an absorbance shift due to a change in the dielectric constant.

Figure 9:
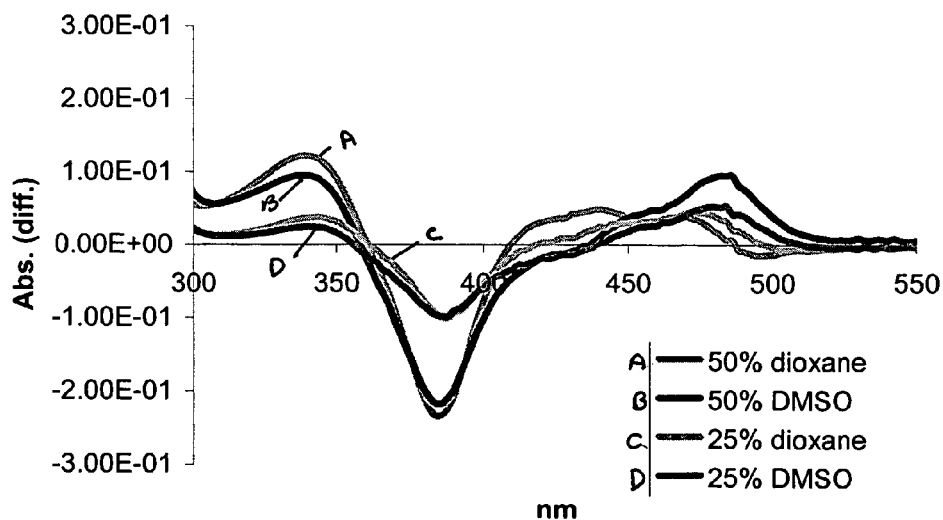
FIG. 9 shows the difference spectra of riboflavin in water compared to riboflavin in water with various amounts of either dioxane or DMSO.

FIG. 9 shows the difference spectra of 120 μM riboflavin in 100% water as compared to riboflavin in water containing various amounts of dioxane or DMSO. The environments approximated by water, water+dioxane, and water+DMSO were chosen to approximate the environment of the major and minor grooves of DNA or loop sections of RNA.

Figure 10:
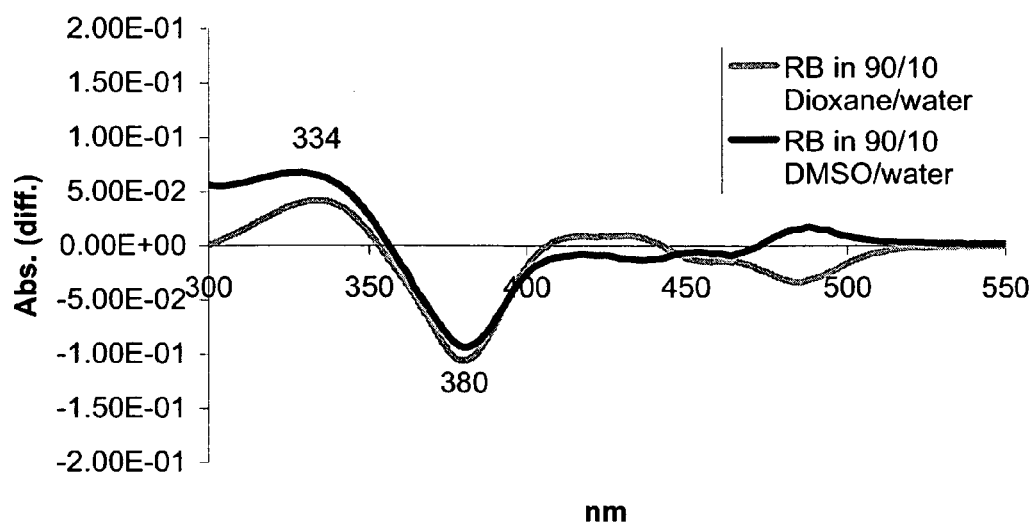
FIG. 10 shows the difference spectra of riboflavin in water or in 10% water+90% dioxane or DMSO.

FIG. 10 shows the difference spectra of 25 μM riboflavin (RB) in 100% water as compared to riboflavin in 10% water+ 90% dioxane or riboflavin in 10% water+90% DMSO.

As can be seen from FIGS. 9 and 10, the shifted absorption spectra indicate that there is no UV-visible shift for the peak at 446 nm. However, intensity of the peak at 374 nm decreases while an increase in the absorption is seen at 334 nm in the presence of dioxane and DMSO. Therefore, a reduction in the dielectric constant appears to shift the 374 nm band further into the UV spectrum, which is consistent with a less-than-expected amount of inactivation in the action spectra at 355 nm and a greater-than-expected amount of inactivation around 330 nm.

Example 5

Using the outcome of these aptamer studies, it may be hypothesized that if the majority of light below 500 nm is

Therefore, an absorption spectrum containing only the flavin-RNA complex could be obtained if the absorption spectrum corresponding to 200-χμM FMN is subtracted from the absorption spectrum of the FMN and aptamer mixture.

Figure 7:
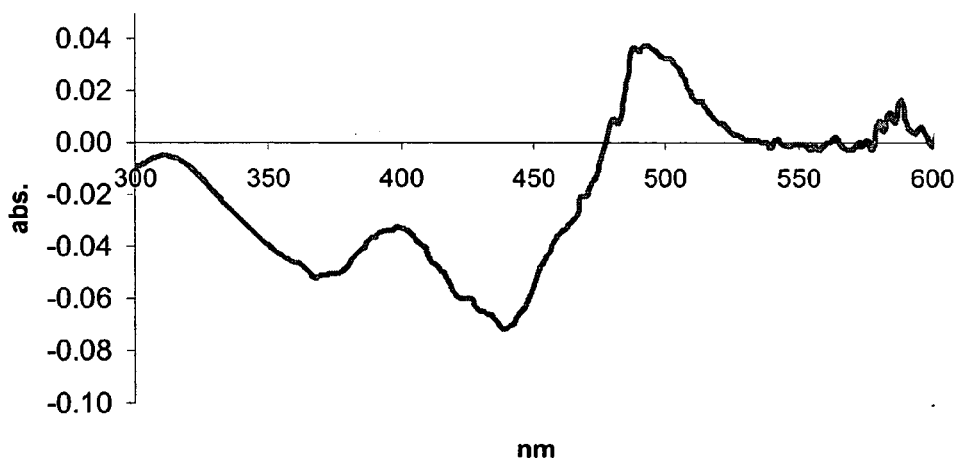
FIG. 7 shows the difference spectra of 200 µM FMN with 200 µM aptamer.

This difference spectrum is shown in FIG. 7.

In an attempt to correct for the subtraction error of the difference spectrum and to obtain a spectrum close to that of pure nucleic acid-bound flavin, the spectrum of free FMN was systematically diminished and subtracted from the spectrum containing the bound flavin. The results of this study are shown in FIG. 8.

Figure 8:
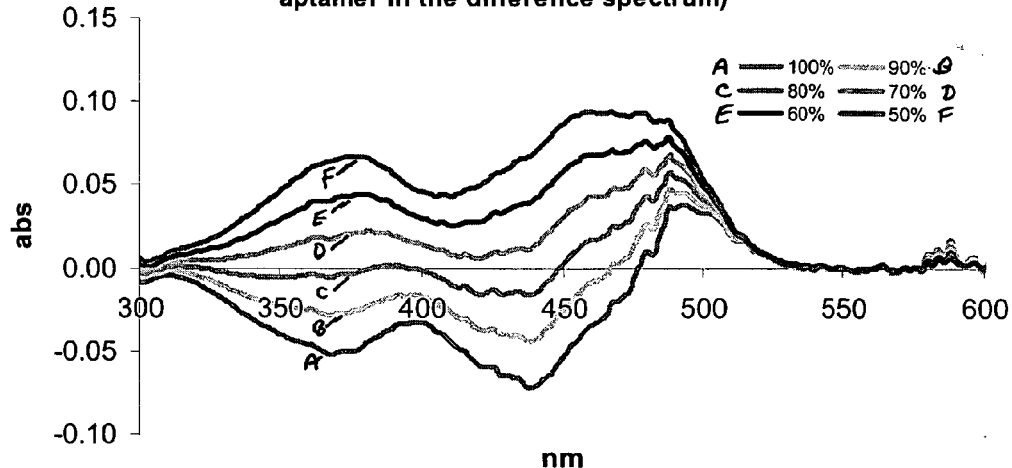
FIG. 8 shows the difference spectra for 200 µm FMN with 200 µM aptamer compared to "scaled" FMN.

For example, in the spectrum shown in FIG. 8, the line listed as "100%", is identical to that in FIG. 7; which shows the difference spectrum of 200 μM FMN and 200 μM aptamer compared to 200 μM FMN. In FIG. 8, the spectrum labeled as "70%", the control (200 μM FMN with no aptamer) has been multiplied by 0.70, which assumes that 30% of the flavin is bound to aptamer ($\chi$=60 μM). This means that the concentration of free FMN in solution (which then should be subtracted) is at a concentration of 140 μM (70% of 200 μM). This spectrum, listed as 70%, will be used as the spectrum of removed, it may be possible to selectively activate only riboflavin which is bound to nucleic acids. Because these studies show that unbound riboflavin is not activated at wavelengths of 500 nm and higher, only riboflavin which is bound to nucleic acids will be activated. Selective activation of bound riboflavin may decrease the potential for indiscriminate damage to cell membranes by the photolysis of unbound riboflavin, which as described above, produces hydrogen peroxide. This effect may be of greater concern in a pathogen reduction procedure of red blood cells due to the high level of oxygen which are present in red blood cells.

The method of this invention requires adding the riboflavin to the fluid to be pathogen reduced. The riboflavin and fluid may also be mixed together. Mixing may occur simply through the addition of riboflavin or a solution containing the riboflavin to the fluid to be decontaminated. Mixing may also occur via mechanical means within the illumination chamber.

Figure 11:
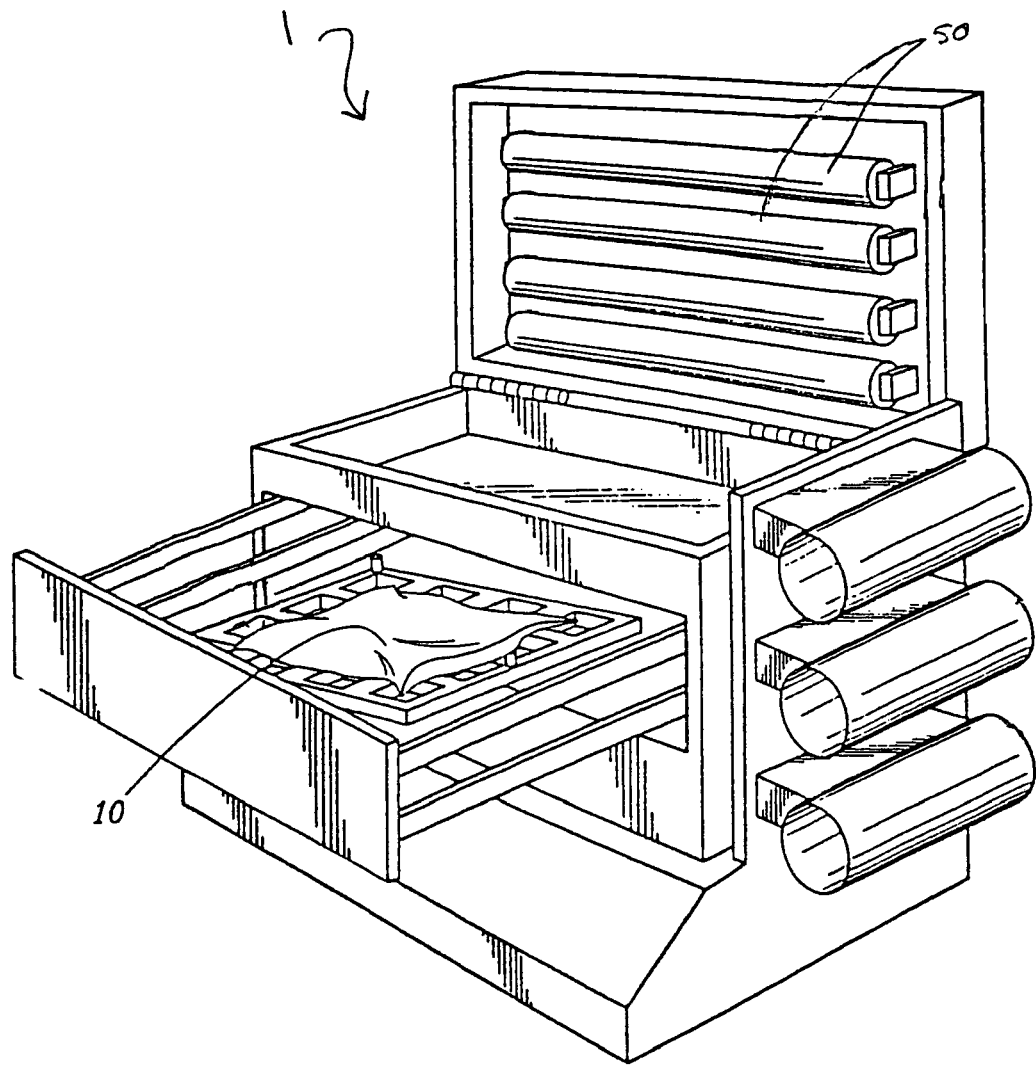
FIG. 11 shows a representative illuminator, which may be used with the present invention.

In an embodiment, the fluid and riboflavin are placed in a photopermeable container such as a blood bag and irradiated in batch mode, preferably while agitating the container to fully distribute the photosensitizer throughout the fluid and expose all the fluid to the radiation. FIG. 11 shows an example of an illuminator 1 with fluid bag 10 which may be used with the present invention.

The fluid containing the photosensitizer is exposed to light at a wavelength of above 500 nm to activate only the riboflavin and pathogenic nucleic acid complex. As discussed above, unbound riboflavin is not activated at this wavelength, so collateral damage to the cells caused by the photolysis of unbound or free riboflavin will be avoided. Light at a wavelength above 500 nm may be obtained by using LEDs which produce light in a very narrow band centered at 500 nm (not shown). Light in a broader spectrum such as that produced by fluorescent bulbs 50 (shown in FIG. 11) may also be used, so long as they are used in conjunction with a filter (not shown) which helps to filter the majority of light below 500 nm out. A filter may also be used to remove light above 550 nm. After the pathogen reduction procedure, the pathogen reduced fluid may then be stored for a period of time before being transfused into a recipient, or may be transfused into a recipient directly after the pathogen reduction procedure.

The invention claimed is:

1. A process for pathogen reduction of a fluid containing blood or blood products which may contain pathogens having nucleic acids comprising:

adding to the fluid a sensitizer containing a flavin moiety;

allowing the sensitizer to bind to the nucleic acid of the pathogens to make a fluid having bound sensitizer and unbound sensitizer; and irradiating the fluid at a wavelength of 500 nm to 550 nm, wherein only the bound sensitizer is activated and the unbound sensitizer is not activated;

thereby reducing the number of pathogens in the fluid.

2. The process of claim 1 wherein the sensitizer containing a flavin moiety is an alloxazine.

3. The process of claim 2 wherein the alloxazine is riboflavin.

4. The process of claim 1, wherein the step of adding sensitizer further comprises adding sensitizer in a concentration between 50 µM and 200 µM.

5. The process of claim 1 wherein the fluid further comprises red blood cells.

6. The process of claim 1 wherein the fluid further comprises platelets.

7. The process of claim 1 wherein the fluid further comprises plasma.

8. The process of claim 1 wherein the step of irradiating further comprises removing light at wavelengths below 500 nm.

9. The process of claim 8 wherein the step of irradiating further comprises removing light at wavelengths above 525 nm.

10. The process of claim 8 wherein the step of irradiating further comprises removing light at wavelengths above 550 nm.

* * * * *